(12) United States Patent
Shibakusa et al.

(10) Patent No.: US 10,369,163 B2
(45) Date of Patent: Aug. 6, 2019

(54) ANTI-FATIGUE COMPOSITION

(71) Applicant: AJINOMOTO CO., INC., Tokyo (JP)

(72) Inventors: Tetsuro Shibakusa, Kawasaki (JP); Mayu Sugita, Kawasaki (JP)

(73) Assignee: AJINOMOTO CO., INC., Tokyo (JP)

(*) Notice: Subject to any disclaimer, the term of this patent is extended or adjusted under 35 U.S.C. 154(b) by 0 days.

(21) Appl. No.: 15/093,207

(22) Filed: Apr. 7, 2016

(65) Prior Publication Data

US 2016/0287616 A1    Oct. 6, 2016

Related U.S. Application Data

(63) Continuation of application No. PCT/JP2014/076989, filed on Oct. 8, 2014.

(30) Foreign Application Priority Data

Oct. 9, 2013 (JP) ................................ 2013-212329

(51) Int. Cl.
| | |
|---|---|
| A61K 31/675 | (2006.01) |
| A61K 31/4172 | (2006.01) |
| A61K 31/4415 | (2006.01) |
| A23L 2/52 | (2006.01) |
| A23L 2/66 | (2006.01) |
| A23L 33/15 | (2016.01) |
| A23L 33/18 | (2016.01) |
| A23L 2/56 | (2006.01) |
| A61K 9/00 | (2006.01) |
| A61K 31/4164 | (2006.01) |
| A23L 33/175 | (2016.01) |

(52) U.S. Cl.
CPC .............. *A61K 31/675* (2013.01); *A23L 2/52* (2013.01); *A23L 2/56* (2013.01); *A23L 2/66* (2013.01); *A23L 33/15* (2016.08); *A23L 33/175* (2016.08); *A23L 33/18* (2016.08); *A61K 9/0053* (2013.01); *A61K 31/4164* (2013.01); *A61K 31/4172* (2013.01); *A61K 31/4415* (2013.01); *A23V 2002/00* (2013.01)

(58) Field of Classification Search
CPC .. A61K 8/673; A61K 31/675; A61K 31/4172; A61K 31/4415
See application file for complete search history.

(56) References Cited

U.S. PATENT DOCUMENTS

| | | | |
|---|---|---|---|
| 6,420,342 B1* | 7/2002 | Hageman | A61K 31/522 514/23 |
| 2002/0103244 A1* | 8/2002 | Matahira | A61K 31/415 514/396 |
| 2006/0093649 A1* | 5/2006 | Murakami | A23L 17/20 424/439 |
| 2006/0115556 A1* | 6/2006 | Foulger | A23L 33/10 426/72 |
| 2006/0211721 A1* | 9/2006 | Roberts | A61K 31/198 514/276 |
| 2009/0018072 A1 | 1/2009 | Scheele | |
| 2011/0245158 A1 | 10/2011 | Scheele | |
| 2013/0108731 A1 | 5/2013 | Scheele | |

FOREIGN PATENT DOCUMENTS

| | | |
|---|---|---|
| CN | 1356103 A | 7/2002 |
| CN | 102318795 A | 1/2012 |
| JP | 9-20661 A | 1/1997 |
| JP | 2001-172189 | 6/2001 |
| JP | 2003-532679 A | 11/2003 |
| JP | 2006-137706 A | 6/2006 |
| JP | 2007-131605 A | 5/2007 |
| WO | WO 01/85178 A1 | 11/2001 |
| WO | WO 2004/032652 A1 | 4/2004 |
| WO | WO 2007/070454 A2 | 6/2007 |

OTHER PUBLICATIONS

Written Opinion dated Dec. 22, 2014 in PCT/JP2014/076989 filed Oct. 8, 2014 (submitting English translation only).

EFSA Panel on Dietetic Products, Nutrition and Allergies (NDA), "Scientific Opinion on the substantiation of health claims related to vitamin B6 and contribution to normal homocysteine metabolism (ID 73, 76, 199), maintenance of normal bone (ID 74), maintenance of normal teeth (ID 74), maintenance of normal hair (ID 74), maintenance of normal skin (ID 74), maintenance of normal nails (ID 74), contribution to normal energy-yielding metabolism (ID 75, 214), contribution to normal psychological functions (ID 77), reduction of tiredness and fatigue (ID 78), and contribution to normal cysteine synthesis (ID 4283) pursuant to Article 13(1) of Regulation (EC) No. 1924/2006" EFSA Journal, vol. 8, No. 10:1759, 2010, 24 Pages.

"Amino san no. kagaku to saishin ouyou gijiyutsu: Frontier of Amino Acid Science and Newly Applications for Better Human Life" Supervisor: Motoni Kadowaki, et al., CMC Publishing Co., Ltd., 2008, pp. 272-283 and Cover Pages.

Osami Kajimoto, et al., "Anti-fatigue medicinal foods development project" Journal of Clinical and Experimental Medicine, vol. 228, No. 6, 2009, pp. 722-726.

New Food Industry, 1994, vol. 36, No. 3, p. 54-64 and partial English Translation (p. 56, Table 2).

Search Report dated May 4, 2017 in Chinese Patent Application No. 201480055604.4 (with English translation).

Jun Zhang, et al., Journal of Taishan Township Enterprise Worker's University, No. 2, 2003, p. 33-34.

Extended Search Report dated Mar. 8, 2017 in European patent Application No. 14851920.0.

Roger W. Purchas, et al., "Quality characteristics and composition of the longissimus muscle in the short-loin from male and female framed red deer in New Zealand", Meat Science, vol. 86, No. 2, Oct. 1, 2010, XP027153735, pp. 505-510.

(Continued)

*Primary Examiner* — Ruth A Davis
(74) *Attorney, Agent, or Firm* — Oblon, McClelland, Maier & Neustadt, L.L.P.

(57) ABSTRACT

Compositions and foods which contain (1) histidine and (2) vitamin B6 and/or carnosine are useful for treating, improving, and recovering from fatigue.

25 Claims, 16 Drawing Sheets

(56) References Cited

OTHER PUBLICATIONS

Yasuyoshi Watanabe, et al., "Effects of chicken essence on recovery from mental fatigue in healthy males", Medical Science Monitor, 2013, vol. 19, XP55347927A, pp. 540-547.
Kin M. Chan, et al., "Endogenous Skeletal Muscle Antioxidants", Critical Reviews in Food Science and Nutrition, vol. 34, No. 4, 1994, XP009193541, pp. 403-426.
Kyung-Jin Yeum, et al., "Profiling histidine dipeptides in plasma and urine after ingesting beef, chicken or chicken broth in humans", Amino Acids, 2010, vol. 38, No. 3, XP19805381A, pp. 847-858.

* cited by examiner

*p<0.05

***p<0.001

*p<0.05、†p<0.1

*p<0.05

*p<0.05、**p<0.01

*p<0.05、**p<0.01

*: p<0.05 vs 3. VB6 group  †: p<0.1 vs 1. solvent group
: p<0.05 vs 1. solvent group  ‡: p<0.1 vs 2. His group
§: p<0.1 vs 3. VB6 group \#: p<0.05 vs 1. solvent group
‡: p<0.1 vs 2. His group
§: p<0.1 vs 3. VB6 group

*p<0.05

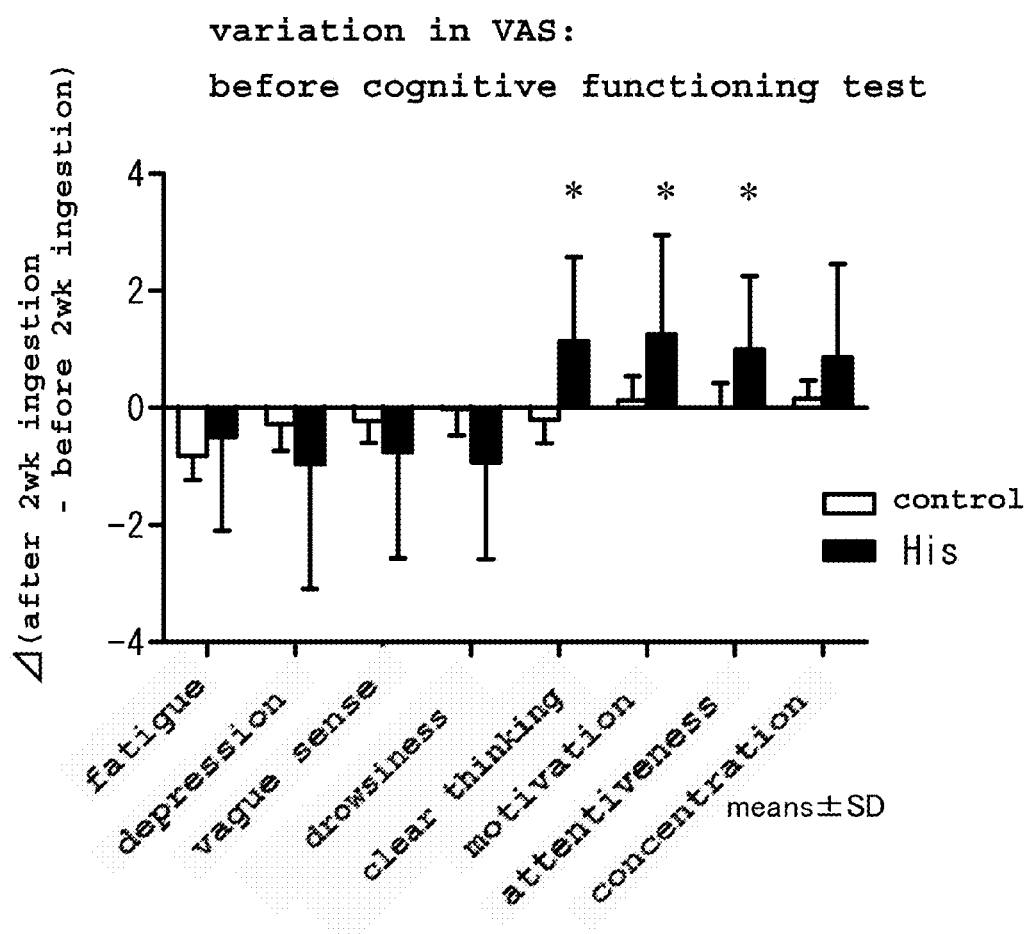

*: p<0.05

ANTI-FATIGUE COMPOSITION

CROSS REFERENCES TO RELATED APPLICATIONS

This application is a continuation of International Patent Application No. PCT/JP2014/076989, filed on Oct. 8, 2014, and claims priority to Japanese Patent Application No. 2013-212329, filed on Oct. 9, 2013, both of which are incorporated herein by reference in their entireties.

BACKGROUND OF THE INVENTION

Field of the Invention

The present invention relates to anti-fatigue compositions, foods which contain such a composition, and uses of such a composition.

Discussion of the Background

Histidine is one kind of basic amino acid, and is an essential amino acid having an imidazoyl group as a heteroaromatic ring in the side chain. Histidine is an amino acid admitted as a food additive, and contained in many foods. For example, histidine is added as a seasoning or flavor-adjusting agent aiming at firm taste, prevention of diffusion of flavor, and the like, and the content thereof is about 50 mg/100 ml at maximum. In relation to the known function of histidine, an anti-fatigue composition containing histidine or histidine hydrochloride is known (see JP-A-2006-137706, which is incorporated herein by reference in its entirety).

Vitamin B6 is one kind of water-soluble vitamin and is a pyridine derivative. Vitamin B6 includes pyridoxine, pyridoxal and pyridoxamine, and they are mutually convertible. They are phosphorylated in the body into pyridoxal 5'-phosphate (PLP) and pyridoxamine 5'-phosphoate, and function as a coenzyme of an enzyme involved in amino acid metabolism such as transamination reaction, decarboxylation reaction and the like. They are also necessary for a reaction to biosynthesize niacin from tryptophan as amino acid, a reaction to biosynthesize glucose 1-phosphate from glycogen, and a reaction to synthesize dopamine and γ-aminobutyric acid as neurotransmitters.

In 2010, vitamin B6 was determined to have the following functions in the "functional claims for food and supplement" issued by EFSA (European Food Safety Authority) (see EFSA Journal 2010; 8(10):1759, which is incorporated herein by reference in its entirety). Normal homocysteine metabolism, maintenance of normal bones/tooth/hair/skin/nail, normal energy-yielding and metabolism, normal psychological function, reduction of tiredness and fatigue, normal cysteine synthesis.

Carnosine is a dipeptide wherein histidine and β alanine are bonded, and is contained in animal-derived foods in large amounts. Carnosine is mainly present in muscles and brain, and a buffering action, an antioxidation action and the like are known (see Amino san no kagaku to saishin ouyou gijiyutsu p. 272-282 CMC Publishing Co., Ltd. 2008, which is incorporated herein by reference in its entirety). It has also been reported that imidazole dipeptide which is a mixture of carnosine and anserine (dipeptide wherein 1 methylhistidine and β alanine are bonded) shows an anti-fatigue effect (see Journal of Clinical and Experimental Medicine, vol. 228, No. 6, p. 722-726, 2009, which is incorporated herein by reference in its entirety).

However, there remains a need for improved anti-fatigue compositions.

SUMMARY OF THE INVENTION

Accordingly, it is one object of the present invention to provide novel anti-fatigue compositions.

It is another object of the present invention to provide novel foods which contain such an anti-fatigue composition.

It is another object of the present invention to provide novel methods of treating and/or preventing fatigue.

When amino acid is added to a food and the like, an influence of the distinct taste of amino acid needs to be considered in some occasions. While histidine is known to have an anti-fatigue effect, since histidine also has a sour taste and a bitter taste, the amount thereof to be added to foods tends to be limited, which sometimes prevents exhibition of a sufficient anti-fatigue action. Therefore, the present invention aims to provide a histidine-containing food capable of affording a sufficient anti-fatigue effect even at a low histidine content, and the like.

These and other objects, which will become apparent during the following detailed description, have been achieved by the inventors' discovery that fatigue can be more effectively improved by using histidine in combination with vitamin B6 and/or carnosine, particularly that a fatigue-improving effect can be obtained even at a low dose at which a single use of each of them cannot provide an effect.

Thus, the present invention provides:

(1) An anti-fatigue composition, comprising (1) histidine and (2) vitamin B6 and/or carnosine in combination.

(1-1) A method of improving fatigue, comprising administering (1) an effective amount of histidine and (2) an effective amount of vitamin B6 and/or carnosine to a subject in need thereof.

(1-2) A composition for improving fatigue, comprising (1) histidine and (2) vitamin B6 and/or carnosine in combination.

(2) The composition of the above-mentioned (1), comprising histidine and vitamin B6 in combination.

(2-1) A method of improving fatigue, comprising administering an effective amount of histidine and an effective amount of vitamin B6 to a subject in need thereof.

(2-2) A composition for improving fatigue, comprising histidine and vitamin B6 in combination.

(3) The composition of the above-mentioned (1), comprising histidine and carnosine in combination.

(3-1) A method of improving fatigue, comprising administering an effective amount of histidine and an effective amount of carnosine to a subject in need thereof.

(3-2) A composition for improving fatigue, comprising histidine and carnosine in combination.

(4) The composition of the above-mentioned (2), wherein the histidine:vitamin B6 is 5:3-350:1.

(4-1) The method of the above-mentioned (2-1), wherein the histidine:vitamin B6 is 5:3 to 350:1.

(4-2) The composition of the above-mentioned (2-2), wherein the histidine:vitamin B6 is 5:3 to 350:1.

(5) The composition of the above-mentioned (4), wherein the histidine is contained at not less than 0.3 g per unit package.

(5-2) The composition of the above-mentioned (4-2), wherein the histidine is contained at not less than 0.3 g per unit package.

(6) The composition of the above-mentioned (4) or (5), wherein the histidine is contained at not less than 0.3 g as an ingestion amount per meal.

(6-2) The composition of the above-mentioned (4-2) or (5-2), wherein the histidine is contained at not less than 0.3 g as an ingestion amount per meal.

(7) The composition of any of the above-mentioned (4)-(6), wherein the vitamin B6 is contained at not less than 0.5 mg as an ingestion amount per meal.

(7-2) The composition of any of the above-mentioned (4-2), (5-2) and (6-2), wherein the vitamin B6 is contained at not less than 0.5 mg as an ingestion amount per meal.

(8) The composition of the above-mentioned (3), wherein histidine:carnosine is 1:4 to 100:1.

(8-2) The composition of the above-mentioned (3-2), wherein histidine:carnosine is 1:4 to 100:1.

(9) A container-packed food, comprising (1) histidine and (2) vitamin B6 and/or carnosine.

(10) The container-packed food of the above-mentioned (9), comprising histidine and vitamin B6.

(11) The container-packed food of the above-mentioned (9), comprising histidine and carnosine.

(12) The container-packed food of the above-mentioned (10), wherein histidine:vitamin B6 is 5:3 to 350:1.

(13) The container-packed food of the above-mentioned (12), wherein the histidine is contained at not less than 0.3 g as an ingestion amount per meal.

(14) The container-packed food of the above-mentioned (12) or (13), wherein the vitamin B6 is contained at not less than 0.5 mg as an ingestion amount per meal.

(15) The container-packed food of any of the above-mentioned (9)-(14), further comprising at least one kind of additive selected from excipient, corrigent and flavor.

(16) The container-packed food of any of the above-mentioned (9)-(15), which is in the form of a solid, semi-solid or liquid.

(17) The container-packed food of any of the above-mentioned (9)-(15), which is in the form of powder, tablet, granule or capsule.

(18) The container-packed food of any of the above-mentioned (9)-(15), which is in the form of slurry, solution, jelly or emulsion.

(19) The container-packed food of any of the above-mentioned (9)-(18), which is in a unit package form per meal.

(20) The container-packed food of any of the above-mentioned (9)-(19), which is for improving fatigue.

(21) A food comprising (1) histidine and (2) vitamin B6 and/or carnosine, which is in a unit package form per meal.

(22) The food of the above-mentioned (21) comprising histidine and vitamin B6, which is in a unit package form per meal.

(23) The food of the above-mentioned (21) comprising histidine and carnosine, which is in a unit package form per meal.

(24) The food of the above-mentioned (22), wherein histidine:vitamin B6 is 5:3 to 350:1.

(25) The food of the above-mentioned (24), wherein histidine is contained at not less than 0.3 g.

(26) The food of the above-mentioned (24) or (25), wherein vitamin B6 is contained at not less than 0.5 mg.

(27) The food of the above-mentioned (23), wherein histidine:carnosine is 1:4 to 100:1.

(28) The food of the above-mentioned (27), wherein histidine is contained at not less than 0.3 g.

(29) The food of any of the above-mentioned (21)-(28), further comprising at least one kind of additive selected from excipient, corrigent and flavor.

(30) The food of any of the above-mentioned (21)-(29), which is in the form of a solid, semi-solid or liquid.

(31) The food of any of the above-mentioned (21)-(29), which is in the form of powder, tablet, granule or capsule.

(32) The food of any of the above-mentioned (21)-(29), which is in the form of slurry, solution, jelly or emulsion.

(33) The food of any of the above-mentioned (21)-(32), which is a food with health claims.

(34) The food of any of the above-mentioned (21)-(33), which is for improving fatigue.

(35) A container-packed drink comprising (1) histidine and (2) vitamin B6 and/or carnosine.

(36) The container-packed drink of the above-mentioned (35), comprising histidine and vitamin B6.

(37) The container-packed drink of the above-mentioned (35), comprising histidine and carnosine.

(38) The container-packed drink of the above-mentioned (36), wherein histidine:vitamin B6 is 5:3 to 350:1.

(39) The container-packed drink of the above-mentioned (38), wherein histidine is contained at not less than 0.3 g as an ingestion amount per meal.

(40) The container-packed drink of the above-mentioned (38), wherein histidine is contained at not less than 1 w/v %.

(41) The container-packed drink of any of the above-mentioned (38)-(40), wherein vitamin B6 is contained at not less than 0.5 mg as an ingestion amount per meal.

(42) The container-packed drink of any of the above-mentioned (35)-(41), which is in a unit package form per meal.

(43) The container-packed drink of any of the above-mentioned (35)-(42), which is a food with health claims.

(44) The container-packed drink of any of the above-mentioned (35)-(43), which is for improving fatigue.

EFFECT OF THE INVENTION

Fatigue (mental fatigue, physical fatigue) can be improved by ingesting the composition of the present invention, comprising (1) histidine and (2) vitamin B6 and/or carnosine. Since the present invention contains amino acid (peptide) and vitamin as active ingredients, it has less fear of causing side effects and is superior in safety, and can also be consecutively used everyday.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 9C shows variation of each index in VAS before cognitive functioning test (CogHealth). *: paired t-test, p<0.05.

DETAILED DESCRIPTION OF THE PREFERRED EMBODIMENTS

Figure 1A:
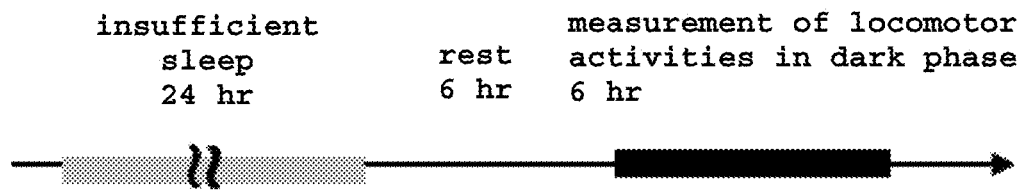
FIG. 1A shows the protocol of generating a fatigue model by burden of insufficient sleep, for the measurement of locomotor activities in the dark phase.

The mode of embodiment of the present invention is explained below.

In the present invention, histidine is an essential amino acid having the following structural formula.

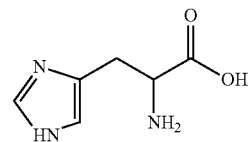 [SMILES: NC(Cc1c[nH]cn1)C(=O)O]

The histidine used in the present invention may be a substance convertible to histidine by hydrolysis. The "substance convertible to histidine by hydrolysis" is a substance that affords histidine by hydrolysis (particularly in vivo hydrolysis), and typical examples thereof include proteins and peptides containing histidine as a constituent unit. A substance that affords histidine by hydrolysis produces histidine by hydrolysis in the body after ingestion, and is expected to provide an effect similar to that obtained when histidine is ingested from the start.

The histidine to be used in the present invention may be one extracted and purified from naturally-present animals, plants and the like, or one obtained by a chemical synthesis method, a fermentation method, an enzyme method or a gene recombination method. Any of L-form, D-form, and DL-form can be used. A commercially available one can be utilized and is preferable since it is convenient.

Vitamin B6 is one kind of water-soluble vitamin having the following structure.

Vitamin B6 includes pyridoxine, pyridoxal, and pyridoxamine, which are mutually convertible. While the vitamin B6 used in the present invention may be any compound as long as a desired effect can be exhibited, it is preferably pyridoxine.

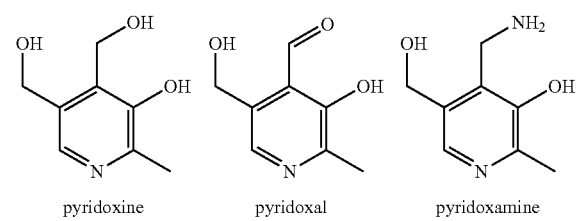

pyridoxine     pyridoxal     pyridoxamine

The vitamin B6 to be used in the present invention may be one extracted and purified from naturally-present animals, plants and the like, or one obtained by a chemical synthesis method. A commercially available one can be utilized and is preferable since it is convenient.

Carnosine is a dipeptide having the following structure, wherein histidine and β alanine are bonded.

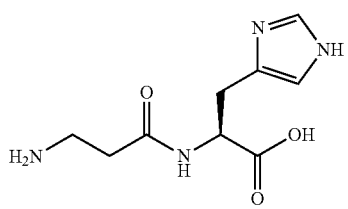 [SMILES: NCCC(=O)N[C@@H](Cc1c[nH]cn1)C(=O)O]

The carnosine to be used in the present invention may be one extracted and purified from naturally-present animals, plants and the like, or one obtained by a chemical synthesis method, a fermentation method, an enzyme method or a gene recombination method. While L-form and D-form (naturally L-form alone) are present due to stereoisomerism, any of them can be used. A commercially available one can be utilized and is preferable since it is convenient.

The carnosine used in the present invention may be a substance convertible to carnosine by hydrolysis. The "substance convertible to carnosine by hydrolysis" is a substance that affords carnosine by hydrolysis (particularly in vivo hydrolysis), and typical examples thereof include proteins and peptides containing carnosine as a constituent unit. A substance that affords carnosine by hydrolysis produces carnosine by hydrolysis in the body after ingestion, and is expected to provide an effect similar to that obtained when carnosine is ingested from the start.

In the present specification, when histidine per se is used as the histidine, the content of histidine in a composition or food is determined taking note of the weight of histidine and, when a substance convertible to histidine by hydrolysis is used, by converting to histidine. When a composition or food contains both histidine and a substance convertible to histidine by hydrolysis, the content of histidine in the composition or food is the total weight of the weight of histidine obtained by converting, by hydrolysis, all substances convertible to histidine by hydrolysis, and histidine presented from the start.

Similarly, when carnosine per se is used as the carnosine, the content of carnosine in a composition or food is determined taking note of the weight of carnosine and, when a substance convertible to carnosine by hydrolysis is used, by converting to carnosine. When a composition or food contains both carnosine and a substance convertible to carnosine by hydrolysis, the content of carnosine in the composition or food is the total weight of the weight of carnosine obtained by converting, by hydrolysis, all substances convertible to carnosine by hydrolysis, and carnosine presented from the start.

Histidine (or substance convertible to histidine by hydrolysis), vitamin B6, and carnosine (or substance convertible to carnosine by hydrolysis) used in the present invention may be in the form of a salt. The form of the salt may be, for example, acid addition salt, salt with a base and the like, and pharmacologically acceptable salt is preferable. Examples of such salt include salts with inorganic acids, salts with organic acids, salts with inorganic bases, and salts with organic bases.

Examples of the salt with an inorganic acid include salts with hydrohalic acid (hydrochloric acid, hydrobromic acid, hydroiodic acid etc.), sulfuric acid, nitric acid, phosphoric acid, and the like.

Examples of the salt with an organic acid include salts with formic acid, acetic acid, propionic acid, oxalic acid, succinic acid, maleic acid, fumaric acid, citric acid, and the like.

Examples of the salt with an inorganic base include salts with alkali metals such as sodium, potassium, lithium and the like, salts with alkaline earth metals such as calcium, magnesium and the like, salt with ammonium and the like.

Examples of the salt with an organic base include salts with ethylenediamine, propylenediamine, ethanolamine, monoalkylethanolamine, dialkylethanolamine, diethanolamine, triethanolamine and the like.

In the present specification, histidine, "substance convertible to histidine by hydrolysis" and a salt thereof are hereinafter generically referred to as histidine, and carnosine, "substance convertible to carnosine by hydrolysis" and a salt thereof are hereinafter generically referred to as carnosine.

One embodiment of the present invention is an anti-fatigue composition containing (1) histidine and (2) vitamin B6/or carnosine in combination and, particularly, an anti-fatigue composition containing histidine and vitamin B6 in combination, and an anti-fatigue composition containing histidine and carnosine in combination are provided.

Another embodiment of the present invention is a method of improving fatigue, comprising administering (1) an effective amount of histidine, and (2) vitamin B6 and/or an effective amount of carnosine to a subject in need thereof and, particularly, a method of improving fatigue, comprising administering (1) an effective amount of histidine and (2) an effective amount of vitamin B6 to a subject in need thereof, and a method of improving fatigue, comprising administering (1) an effective amount of histidine, and (2) an effective amount of carnosine to a subject in need thereof are provided.

Another embodiment of the present invention is a composition containing (1) histidine and (2) vitamin B6 and/or carnosine in combination for improving fatigue and, particularly, a composition containing histidine and vitamin B6 in combination for improving fatigue, and a composition containing histidine and carnosine in combination for improving fatigue are provided.

The anti-fatigue composition, the method of improving fatigue, and the composition for improving fatigue of the present invention may use histidine in combination with vitamin B6, histidine in combination with carnosine, or histidine in combination with vitamin B6 and carnosine. Preferably, they use histidine in combination with vitamin B6. The combination ratio of histidine and vitamin B6 can be appropriately determined within the range where an anti-fatigue effect can be obtained.

Preferable combination ratios include histidine:vitamin B6=5:3 to 350:1, 15:1 to 350:1, 30:1 to 350:1, 60:1 to 350:1, and 90:1 to 350:1. Other preferable combination ratios include histidine:vitamin B6=5:3 to 350:1, 5:3 to 300:1, 5:3 to 240:1, and 5:3 to 120:1. Still other preferable combination ratios include histidine:vitamin B6=5:3 to 350:1, 15:1 to 300:1, 30:1 to 240:1, 60:1 to 120:1, and 90:1 to 120:1.

The combination ratio of histidine and carnosine can also be determined appropriately within the range where an anti-fatigue effect can be obtained.

Preferable combination ratios include histidine:carnosine=1:4 to 100:1, 1:2 to 100:1, and 1:1 to 100:1. Other preferable combination ratios include histidine:carnosine=1:4 to 100:1, 1:4 to 50:1, and 1:4 to 30:1. Other preferable combination ratios include histidine:carnosine=1:4 to 100:1, 1:2 to 50:1, and 1:1 to 30:1.

When both vitamin B6 and carnosine are administered for combined use with histidine, the dose of vitamin B6 and/or carnosine can be reduced as compared to a single administration thereof.

In the composition of the present invention, the administration form of (1) histidine and (2) vitamin B6/or carnosine is not particularly limited, and (1) and (2) only need to be combined at the time of administration. Examples of such administration form include:

(A) administration as a single composition simultaneously containing (1) and (2), (B) simultaneous administration of two kinds (or 3 kinds) of compositions separately containing (1) and (2) by the same administration route, (C) administration of two kinds (or 3 kinds) of compositions separately containing (1) and (2) by the same administration route in a staggered manner, (D) simultaneous administration of two kinds (or 3 kinds) of compositions separately containing (1) and (2) by different administration routes, (E) administration of two kinds (or 3 kinds) of compositions separately containing (1) and (2) by different administration routes in a staggered manner and the like.

In 2010, the Japanese Society of Fatigue Science reported the definition of "fatigue" as "fatigue is decline in the ability for activity of the body accompanied by a peculiar sense of discomfort and a desire to rest, caused by excessive mental and psychological activities, or disease(s)". That is, "fatigue" is defined to be reduction of performance. In the present invention, "fatigue" is intended to mean both mental fatigue and physical fatigue. The term "anti-fatigue" or "fatigue improvement" refers to a fatigue recovery action that promptly recovers the body from the state of fatigue, effect of relieving fatigue when physical burden and mental burden (including burden of insufficient sleep and the like) are applied, or an action to relieve stresses felt daily such as copiopia, mental fatigue, or mental insufficiency and the like, and further, improve efficiency of brain work.

The anti-fatigue composition of the present invention refers to a composition that improves or recovers decline in the ability for activity of the body accompanied by a peculiar sense of discomfort and a desire to rest, caused by excessive mental and psychological activities, or a disease.

The anti-fatigue effect can be evaluated by a method known per se. Examples of such methods include subjective evaluation methods such as visual analog scale (VAS), Profile of Mood States (POMS) and the like, and objective evaluation methods such as cognitive functioning test •CogHealth (Coghealth: manufactured by Cogstate Ltd., Health Solution, Inc. provide) capable of measuring a brain function which will be decreased due to fatigue and aging.

When VAS is utilized, for example, the level of fatigue can be judged by evaluating whether the test subject shows low scores of positive index (clear thinking, motivation, attentiveness or concentration), or high score of negative index (depression or drowsiness). When, for example, scores are measured before and after continuous ingestion or single ingestion of a test sample for a given period, and the score of positive index significantly increases or the score of negative index significantly decreases after sample ingestion, the fatigue can be evaluated to have been improved. Particularly, one or more indices selected from the group consisting of clear thinking, motivation, attentiveness, concentration, depression and drowsiness can be significantly improved by ingesting the composition of the present invention.

When POMS is utilized, for example, the level of fatigue can be judged by evaluating whether the test subject shows low scores of positive index (vigor), or high score of negative index (anxiety, depression, anger, fatigue or confusion). More specifically, when the score of fatigue factor (F factor) is not less than 16 by subjective evaluation by POMS, the presence of fatigue is admitted. When, for example, scores are measured before and after continuous ingestion or single ingestion of a test sample for a given period, and the score of positive index significantly increases or the score of negative index significantly decreases after sample ingestion, the fatigue can be evaluated to have been improved. Particularly, the indices of fatigue and confusion can be significantly improved by ingesting the composition of the present invention.

When CogHealth is utilized, for example, the level of fatigue can be judged by evaluating whether the accuracy rate is low or the reaction time is long in a simple reaction or delayed recall. Furthermore, for example, when a test is performed after continuous ingestion of a test sample or placebo for a given period, and the accuracy rate significantly increases or the reaction time significantly decreases in a test sample ingestion group in a simple reaction or delayed recall as compared to placebo ingestion group, the fatigue can be evaluated to have been improved by ingesting the test sample. Particularly, the reaction time in the delayed recall can be significantly lowered by ingesting the composition of the present invention.

For evaluation of fatigue and anti-fatigue in animals, a decrease in performance and recovery of the decrease (change in locomotor activities, alternation behavior showing short-working memory in the below-mentioned Y-maze test etc. as indices) only need to be measured by a method known per se, after applying a physical burden (treadmill, swimming etc.), mental burden (restraint stress etc.), or composite stress burden including both (insufficient sleep in water bed etc.). For example, a data acquisition analysis system containing an infrared sensor (e.g., NS-DAS-32 (NeuroScience, Inc) and the like) can be utilized. For example, measurement is performed after continuous ingestion of a test sample or a control sample for a given period by a target with fatigue induced by various burdens and, when a decrease in the performance (decrease in spontaneous amount and alternation behavior) is improved in a test sample ingestion group as compared to a control sample ingestion group, the fatigue can be evaluated to have been improved/recovered by the ingestion of the test sample.

The anti-fatigue composition of the present invention may be solid or semi-solid, or liquid such as powder, tablet, granule, capsule, slurry, solution, jelly, emulsion, and the like.

As one embodiment of the anti-fatigue composition of the present invention, a composition containing histidine:vitamin B6 at the above-mentioned combination ratio, and histidine at not less than 0.3 g, preferably not less than 0.5 g, more preferably not less than 0.7 g, further preferably not less than 1 g, as an ingestion amount per meal is provided. From the aspects of eating experiences obtained from known findings (Food Safety Commission of Japan, Feed/Fertilizer, etc. Expert Committee, April 2010, exempted evaluation report histidine, safety and effectiveness information of "health food" (National Institute of Health and Nutrition HP https://hfnet.nih.go.jp/) which is incorporated herein by reference in its entirety) and easiness of packaging and ingestion, the ingestion amount per meal of histidine is preferably not more than 23 g, more preferably not more than 4 g. In the present invention, since the effect of combined use of vitamin B6 on the anti-fatigue effect can be expected, the ingestion amount per meal of histidine can be further reduced and, for example, an anti-fatigue composition containing not more than 3 g, preferably not more than 2 g, of histidine as an ingestion amount per meal can be provided.

In one embodiment of the anti-fatigue composition of the present invention, a composition containing histidine:vitamin B6 at the above-mentioned combination ratio, and histidine at not less than 0.3 g, preferably not less than 0.5 g, more preferably not less than 0.7 g, further preferably not less than 1 g, per unit package is provided. Specifically, an anti-fatigue composition packaged as an ingestion amount per meal as one unit is provided.

In another embodiment of the anti-fatigue composition of the present invention, a composition containing histidine:vitamin B6 at the above-mentioned combination ratio, and vitamin B6 at not less than 0.5 mg, preferably not less than 2 mg, more preferably not less than 4 mg, further preferably not less than 6 mg, further preferably not less than 8 mg, further preferably not less than 10 mg, further preferably not less than 15 mg, is provided. The ingestion amount of vitamin B6 per meal is generally less than 300 mg, preferably not more than 100 mg, since ingestion of an amount exceeding this level does not remarkably enhance the anti-fatigue effect.

The anti-fatigue composition of the present invention can be provided as a food. In the present specification, food is a concept widely encompassing oral ingestible matters, and includes not only what is called "food" but also a drink, health aid food, food with health claims, supplement, and the like. In the present invention, an anti-fatigue composition provided as food, food such as food in a unit package form per meal and the like, container-packed food, and container-packed drink are sometimes to be generically referred to as the food of the present invention. In addition, the anti-fatigue composition of the present invention can be provided as an agent. In the present specification, the agent excludes pharmaceutical products, and is ingested for a particular purpose, different from those daily ingested to retain nutrition of the body.

The form of the food of the present invention is not particularly limited, and may be solid or semi-solid, or liquid such as powder, tablet, granule, slurry, capsule, solution, jelly, emulsion, and the like.

The form of histidine, and vitamin B6 and/or carnosine to be contained in the food of the present invention is not particularly limited, and may be powder or granule, slurry, tablet confectionery, capsule, solution, jelly, or emulsion. Of these, granule and powder are preferable, in view of easy portability and easy packaging. In addition, solution, jelly, and slurry are also preferable in view of easy ingestion.

In the present invention, examples of the unit package form per meal include a form that defines a given amount in a pack, package, bottle, etc. in the case of drink, confectionery, jelly, pudding, yogurt, and the like, and package and the like can define a given amount in the case of granular, powdery and slurry foods. Alternatively, a form such as a container and the like indicating the ingestion amount per meal can be mentioned. As used herein, confectionery refers to favorite foods such as sweet stuff and the like, which are eaten other than meals, and examples thereof include candy, chewing gum, tablet confectionery, chocolate, shake, ice, and the like.

The present invention provides a food comprising (1) histidine and (2) vitamin B6/or carnosine, which is in a unit package form per meal, particularly, a food comprising histidine and vitamin B6, which is in a unit package form per meal, and a food comprising histidine and carnosine, which is in a unit package form per meal.

The food in a unit package form per meal of the present invention may contain histidine and vitamin B6, or histidine and carnosine, or histidine and vitamin B6, and carnosine. Preferred is one containing histidine and vitamin B6.

The combination ratio of histidine and vitamin B6 can be appropriately determined within the range where an anti-fatigue effect can be obtained.

Preferable combination ratios include histidine:vitamin B6=5:3 to 350:1, 15:1 to 350:1, 30:1 to 350:1, 60:1 to 350:1, m and 90:1 to 350:1. Other preferable combination ratios include histidine:vitamin B6=5:3 to 350:1, 5:3 to 300:1, 5:3 to 240:1, and 5:3 to 120:1. Still other preferable combination ratios include histidine:vitamin B6=5:3 to 350:1, 15:1 to 300:1, 30:1 to 240:1, 60:1 to 120:1, and 90:1 to 120:1.

The combination ratio of histidine and carnosine can also be determined appropriately within the range where an anti-fatigue effect can be obtained.

Preferable combination ratios include histidine:carnosine=1:4 to 100:1, 1:2 to 100:1, and 1:1 to 100:1. Other preferable combination ratios include histidine:carnosine=1:4 to 100:1, 1:4 to 50:1, and 1:4 to 30:1. Other preferable combination ratios include histidine:carnosine=1:4 to 100:1, 1:2 to 50:1, and 1:1 to 30:1.

When both vitamin B6 and carnosine are contained in addition to histidine, the content of vitamin B6 and/or carnosine can be reduced as compared to a single administration thereof.

As one embodiment of the food in a unit package form per meal of the present invention, a composition containing histidine:vitamin B6 at the above-mentioned combination ratio, and histidine at not less than 0.3 g, preferably not less than 0.5 g, more preferably not less than 0.7 g, further preferably not less than 1 g, as an ingestion amount per meal is provided. From the aspects of eating experiences obtained from known finding (mentioned above) and easiness of packaging and ingestion, the ingestion amount per meal of histidine is preferably not more than 23 g, more preferably not more than 4 g. In the present invention, since the effect of combined use of vitamin B6 on the anti-fatigue effect can be expected, the ingestion amount per meal of histidine can be further reduced and, for example, a food containing not more than 3 g, preferably not more than 2 g, of histidine as an ingestion amount per meal can be provided.

In one embodiment of the food in a unit package form per meal of the present invention, a food containing histidine:vitamin B6 at the above-mentioned combination ratio, and histidine at not less than 0.3 g, preferably not less than 0.5 g, more preferably not less than 0.7 g, further preferably not less than 1 g, per unit package is provided.

In another embodiment of the food in a unit package form per meal of the present invention, a food containing histidine:vitamin B6 at the above-mentioned combination ratio, and vitamin B6 at not less than 0.5 mg, preferably not less than 2 mg, more preferably not less than 4 mg, further preferably not less than 6 mg, further preferably not less than 8 mg, further preferably not less than 10 mg, further preferably not less than 15 mg, is provided. The ingestion amount of vitamin B6 per meal is generally less than 300 mg, preferably not more than 100 mg, since ingestion of an amount exceeding this level does not remarkably enhance the anti-fatigue effect.

Another embodiment of the present invention is a container-packed food, comprising (1) histidine and (2) vitamin B6 and/or carnosine, particularly a container-packed food comprising histidine and vitamin B6, and a container-packed food comprising histidine and carnosine. The "food" in the container-packed food of the present invention is, for example, the above-mentioned anti-fatigue composition provided as food. It can be produced by injecting or filling the food in a desired container.

The container-packed food of the present invention may contain histidine and vitamin B6, or histidine and carnosine, or histidine and vitamin B6 and carnosine. Preferred is one containing histidine and vitamin B6. The combination ratio of histidine and vitamin B6 in the food can be appropriately determined within the range where an anti-fatigue effect can be obtained.

Preferable combination ratios include histidine:vitamin B6=5:3 to 350:1, 15:1 to 350:1, 30:1 to 350:1, 60:1 to 350:1, and 90:1 to 350:1. Other preferable combination ratios include histidine:vitamin B6=5:3 to 350:1, 5:3 to 300:1, 5:3 to 240:1, and 5:3 to 120:1. Still other preferable combination ratios include histidine:vitamin B6=5:3 to 350:1, 15:1 to 300:1, 30:1 to 240:1, 60:1 to 120:1, and 90:1 to 120:1.

The combination ratio of histidine and carnosine can also be determined appropriately within the range where an anti-fatigue effect can be obtained.

Preferable combination ratios include histidine:carnosine=1:4 to 100:1, 1:2 to 100:1, and 1:1 to 100:1. Other preferable combination ratios include histidine:carnosine=1:4 to 100:1, 1:4 to 50:1, and 1:4 to 30:1. Other preferable combination ratios include histidine:carnosine=1:4 to 100:1, 1:2 to 50:1, and 1:1 to 30:1.

As one embodiment of the container-packed food of the present invention, a container-packed food containing histidine:vitamin B6 at the above-mentioned combination ratio, and histidine at not less than 0.3 g, preferably not less than 0.5 g, more preferably not less than 0.7 g, further preferably not less than 1 g, as an ingestion amount per meal is provided. From the aspects of eating experiences obtained from known finding (mentioned above) and easiness of packaging and ingestion, the ingestion amount per meal of histidine is preferably not more than 23 g, more preferably not more than 4 g. In the present invention, since the effect of combined use of vitamin B6 on the anti-fatigue effect can be expected, the ingestion amount per meal of histidine can be further reduced and, for example, a container-packed food containing not more than 3 g, preferably not more than 2 g, of histidine as an ingestion amount per meal can be provided.

In another embodiment of the container-packed food of the present invention, a container-packed food containing histidine:vitamin B6 at the above-mentioned combination ratio, and vitamin B6 at not less than 0.5 mg, preferably not less than 2 mg, more preferably not less than 4 mg, further preferably not less than 6 mg, further preferably not less than 8 mg, further preferably not less than 10 mg, further preferably not less than 15 mg, is provided. The ingestion amount of vitamin B6 per meal is generally less than 300 mg, preferably not more than 100 mg, since ingestion of an amount exceeding this level does not remarkably enhance the anti-fatigue effect.

Another embodiment of the present invention is a container-packed drink, comprising (1) histidine and (2) vitamin B6 and/or carnosine, particularly a container-packed drink comprising histidine and vitamin B6, and a container-packed drink comprising histidine and carnosine. The container-packed drink of the present invention is one embodiment of the above-mentioned container-packed food of the present invention. The "drink" in the container-packed drink of the present invention includes, for example, the above-mentioned anti-fatigue composition provided as a drink, specifically, drinks such as tea drinks (e.g., green tea, oolong tea, black tea, etc.), alcohol drinks (e.g., beer, wine, sake, distilled spirits, ume (Japanese plum) wine, low-malt beer, whiskey, brandy, etc.), beverage (e.g., sports drinks, isotonic drinks, mineral water, coffee drinks, etc.), juice (e.g., fruit juice, vegetable juice, etc.) and the like, liquid seasoning (e.g., soy sauce, vinegar, liquor, sweet sake for seasoning, soup stock, etc.), liquid supplement (e.g., nutritional supplement drink, beauty drink, energy drink, etc.), and the like. It can be produced by injecting or filling the drink in a desired container. The drink includes not only those served as a solution, a suspension and the like, but also those served for drinking after extraction and dissolution such as tea leaves, coffee beans, powder drinks, and the like.

The container-packed drink of the present invention may contain histidine and vitamin B6, or histidine and carnosine, or histidine and vitamin B6 and carnosine. Preferred is one containing histidine and vitamin B6. The combination ratio of histidine and vitamin B6 in the drink can be appropriately determined within the range where an anti-fatigue effect can be obtained. Preferable combination ratios include histidine:vitamin B6=5:3 to 350:1, 15:1 to 350:1, 30:1 to 350:1, 60:1 to 350:1, and 90:1 to 350:1. Other preferable combination ratios include histidine:vitamin B6=5:3 to 350:1, 5:3 to 300:1, 5:3 to 240:1, and 5:3 to 120:1. Still other preferable combination ratios include histidine:vitamin B6=5:3 to 350:1, 15:1 to 300:1, 30:1 to 240:1, 60:1 to 120:1, and 90:1 to 120:1.

The combination ratio of histidine and carnosine can also be determined appropriately within the range where an anti-fatigue effect can be obtained. Preferable combination ratios include histidine:carnosine=1:4 to 100:1, 1:2 to 100:1, and 1:1 to 100:1. Other preferable combination ratios include histidine:carnosine=1:4 to 100:1, 1:4 to 50:1, and 1:4 to 30:1.

Other preferable combination ratios include histidine:carnosine=1:4 to 100:1, 1:2 to 50:1, and 1:1 to 30:1.

As one embodiment of the container-packed drink of the present invention, a container-packed drink containing histidine:vitamin B6 at the above-mentioned combination ratio, and histidine at not less than 0.3 g, preferably not less than 0.5 g, more preferably not less than 0.7 g, further preferably not less than 1 g, as an ingestion amount per meal is provided. From the aspects of eating experiences obtained from known finding (mentioned above) and easiness of packaging and ingestion, the ingestion amount per meal of histidine is preferably not more than 23 g, more preferably not more than 4 g. In the present invention, since the effect of combined use of vitamin B6 on the anti-fatigue effect can be expected, the ingestion amount per meal of histidine can be further reduced and, for example, a container-packed drink containing not more than 3 g, preferably not more than 2 g, of histidine as an ingestion amount per meal can be provided.

As one embodiment of the container-packed drink of the m present invention, a drink containing histidine:vitamin B6 at the above-mentioned combination ratio, and histidine at a concentration of not less than 1 w/v % can be ingested in necessary quantities for necessary times. A container-packed drink preferably at not less than 3 w/v %, more preferably not less than 5 w/v %, is provided. A container-packed drink generally at not more than 30 w/v %, preferably not more than 20 w/v %, more preferably not more than 17 w/v %, further preferably not more than 10 w/v %, is provided.

In another embodiment of the container-packed drink of the present invention, a container-packed drink containing histidine:vitamin B6 at the above-mentioned combination ratio, and vitamin B6 at not less than 0.5 mg, preferably not less than 2 mg, more preferably not less than 4 m, further preferably not less than 6 mg, further preferably not less than 8 mg, further preferably not less than 10 mg, further preferably not less than 15 mg, is provided. The ingestion amount of vitamin B6 per meal is generally less than 300 mg, preferably not more than 100 mg, since ingestion of an amount exceeding this level does not remarkably enhance the anti-fatigue effect.

A container to be used for the container-packed food or container-packed drink of the present invention is appropriately selected according to the object. Generally, a can, bottle, PET bottle, paper container, aluminum pouch, and the like can be mentioned. The volume is not particularly limited, and one or more units may be housed in one container wherein ingestion amount per meal is one unit, or concentrated food/drink may be filled in a container.

The histidine, and vitamin B6 and/or carnosine contained in the food of the present invention being "slurry" means that solid histidine, and vitamin B6 and/or carnosine are suspended in a liquid medium. A part of histidine, and vitamin B6 and/or carnosine may be dissolved in the above-mentioned medium.

In the food of the present invention, the ingestion form of (1) histidine and (2) vitamin B6/or carnosine is not particularly limited, and (1) and (2) only need to be combined at the time of ingestion. Examples of such administration form include (A) ingestion as a single food simultaneously containing (1) and (2), (B) simultaneous ingestion of two kinds (or 3 kinds) of foods separately containing (1) and (2) by the same administration route, (C) ingestion of two kinds (or 3 kinds) of foods separately containing (1) and (2) by the same administration route in a staggered manner, (D) simultaneous ingestion of two kinds (or 3 kinds) of foods separately containing (1) and (2) by different administration routes, (E) ingestion of two kinds (or 3 kinds) of foods separately containing (1) and (2) by different administration routes in a staggered manner, and the like.

Examples of the application target of the food of the present invention include experiment animals such as rodents (e.g., mouse, rat, hamster, guinea pig, and the like), rabbit and the like, pets such as a dog, cat, and the like, domestic animals and poultry such as bovine, swine, goat, horse, sheep, chicken, and the like, primates such as monkey, orangutan, chimpanzee, and the like, humans, and the like, and human is particularly preferable. For application to an animal other than human, the dose of the food of the present invention can be appropriately moderated based on the general description of the dose for human, which is described in the present specification, and further considering the body weight or size of the animal, or the condition, sensitivity and the like of the administration subject at the time of administration.

The food of the present invention is preferably food with health claims, more preferably food for improving fatigue.

The food of the present invention can contain various additives in an attempt to provide the same in a form easier to take. Specifically, a corrigent, flavor, excipient, lubricant, and the like can be mentioned, and any additive can be utilized as long as addition to food is admitted. Examples of the corrigent include souring agents such as ascorbic acid, tartaric acid, citric acid, malic acid and salts of these, and the like, sweeteners such as aspartame, stevia, sucralose, glycyrrhizinic acid, thaumatin, acesulfame potassium, saccharin, saccharin sodium and the like, and the like. Examples of the flavor include synthetic flavor compounds such as L-menthol and the like, citrus essential oils such as orange, lemon, lime, grapefruit, and the like, plant essential oils such as a flower essential oil, peppermint oil, spearmint oil, spice oil, and the like, and the like. Examples of the excipient include lactose, sucrose, D-mannitol, starch, cornstarch, crystalline cellulose, light anhydrous silicic acid, and the like. Examples of the lubricant include magnesium stearate, calcium stearate, talc, colloidal silica, and the like.

Other features of the invention will become apparent in the course of the following descriptions of exemplary embodiments which are given for illustration of the invention and are not intended to be limiting thereof.

EXAMPLES

Experimental Example 1: Verification of Influence of Burden of Insufficient Sleep on Locomotor Activities in the Dark Phase (Fatigue Index)

Using CD2F1 mice (9-week-old or older) (CHARLES RIVER LABORATORIES JAPAN, INC) divided into a control group and a group burdened by insufficient sleep, an experiment was performed as shown in the experiment protocol of FIG. 1A.

The insufficient sleep-burdened group was burdened by insufficient sleep for 24 hr by filling water in the breeding cage at the depth of 0.5 cm. The burden was released at 6 hr from the start of the light phase, and the mice were placed back in the home cage and allowed to rest for 6 hr. The control group was reared without burden in the home cage. Thereafter, they were transferred into a cage set under a locomotor activity measurement infrared sensor (Digital acquisition system; NS-DAS-32, Neuroscience Inc, Tokyo, Japan) under fasting and water-deprivation. The locomotor activities in the former half (6 hr) of the dark phase were measured and the data was collected by a multidigital counter (Neuroscience Inc, Tokyo, Japan).

Figure 1B:
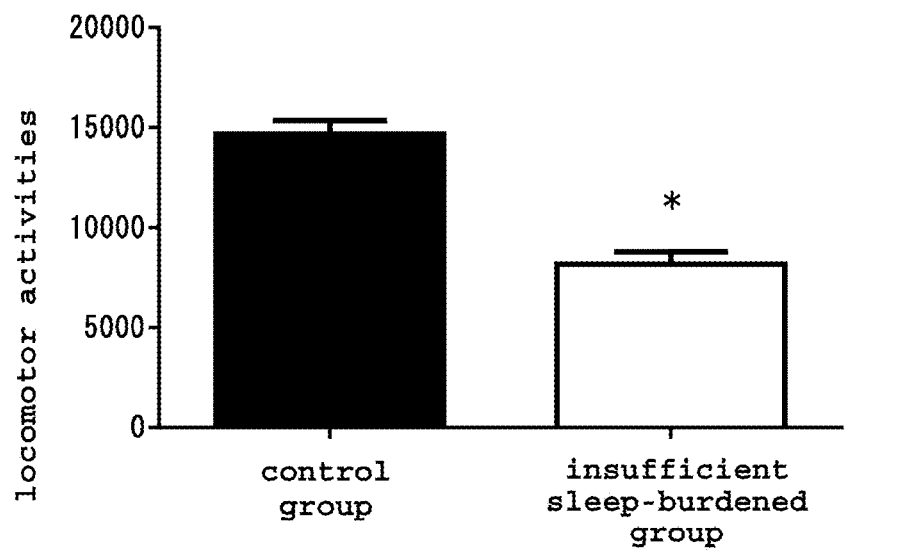
FIG. 1B shows cumulative locomotor activities for the former half (6 hr) of the dark phase. *: t-test, $p<0.05$.

The results are shown in FIG. 1B. Since the insufficient sleep-burdened group showed a decrease in the locomotor activities in the former half of the dark phase (fatigue index) as compared to the control group, it was clarified that burden of insufficient sleep decreases the performance or induces fatigue.

Experimental Example 2: Verification of Influence of Burden of Insufficient Sleep on Short-Working Memory (Fatigue Index)

Figure 2A:
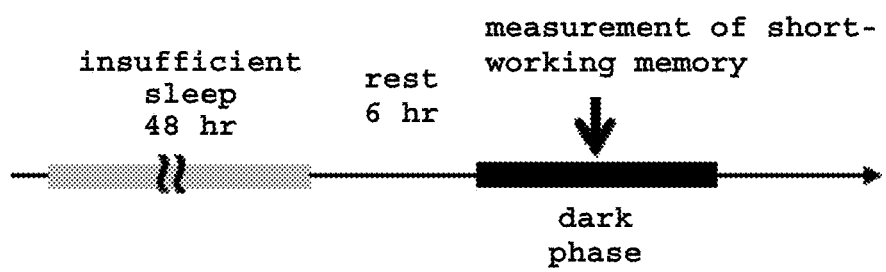
FIG. 2A shows the protocol for generating a fatigue model by burden of insufficient sleep, for the measurement of short-working memory.

Using CD2F1 mice (9-week-old or older) (CHARLES RIVER LABORATORIES JAPAN, INC) divided into a control group and an insufficient sleep-burdened group, an experiment was performed as shown in the experiment protocol of FIG. 2A.

The insufficient sleep-burdened group was burdened by insufficient sleep for 48 hr by filling water in the breeding cage at the depth of 0.5 cm. The burden was released 6 hr after the start of the light phase, and the mice were placed back in the home cage and allowed to rest for 6 hr. The control group was reared without burden in the home cage. A Y-maze test was performed at 3 hr from the start of the dark phase, and short-working memory was measured.

Figure 2B:
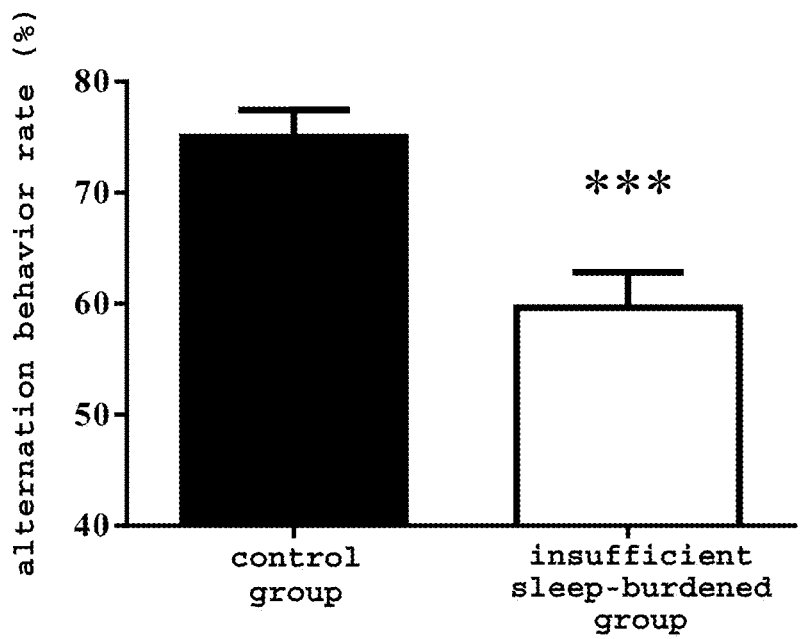
FIG. 2B shows the measurement results of alternation behavior. ***: t-test, $p<0.001$.

The results are shown in FIG. 2B. Since the insufficient sleep-burdened group showed a decrease in the short-working memory (fatigue index) as compared to the control group, it was clarified that burden of insufficient sleep decreases the performance or induces fatigue.

Figure 3A:
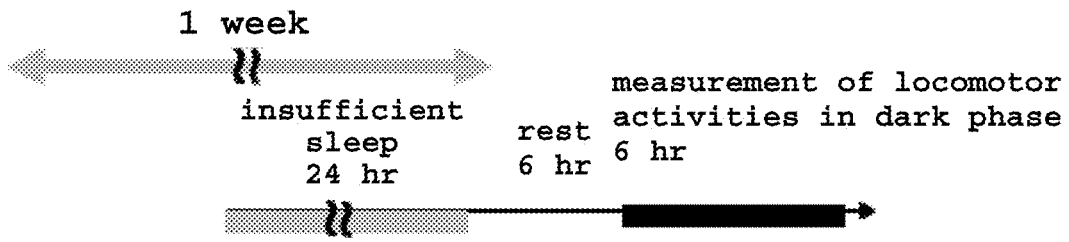
FIG. 3A shows the protocol for verifying the effect of the ingestion of histidine (His) and/or test substance X on the improvement of a decrease in the locomotor activities in the dark phase (fatigue index) of mouse after burden of insufficient sleep.

Example 1: Verification of Effect of Administration of Histidine (His) and Test Substance X on Decrease in Locomotor Activities in the Dark Phase (Fatigue Index) after Burden of Insufficient Sleep Using CD2F1 mice (9-week-old or older) (CHARLES RIVER LABORATORIES JAPAN, INC) in the group constitution shown in Table 1, the effect was verified as shown in the experiment protocol of FIG. 3A.

TABLE 1

| group No. | group name | His | test substance X |
|---|---|---|---|
| 1. | solvent group | − | − |
| 2. | His group | + | − |
| 3. | test substance X group | − | + |
| 4. | combined use group | + | + |

The His group and the combined use group were allowed to drink each solution freely for one week so that the dose of His would be 500 mg/kg/day. The test substance X group and the combined use group were made to ingest test substance X mixed in a feed or drinking water for one week so that the ingestion amount of Table 3 would be met. As the feed, a feed having the composition of Table 2 was used.

TABLE 2

| Feed Composition | |
|---|---|
| composition | composition (%) |
| casein | 20.0000 |
| L-cystine | 0.3000 |
| cornstarch | 39.7486 |
| pregelatinized cornstarch | 13.2000 |
| sucrose | 10.0000 |
| soybean oil | 7.0000 |
| cellulose powder | 5.0000 |
| mineral mix (AIN-93G-MX) | 3.5000 |
| vitamin mix (AIN-93-MX) | 1.0000 |
| choline bitartrate | 0.2500 |
| tertiary butylhydroquinone | 0.0014 |

After ingestion of His and test substance X for one week, insufficient sleep was burdened for 24 hr by filling water in the breeding cage at the depth of 0.5 cm. The burden was released at 6 hr from the start of the light phase, and the mice were placed back in the home cage and allowed to rest for 6 hr. Thereafter, they were transferred into a cage set under a locomotor activity measurement infrared sensor (Digital m acquisition system; NS-DAS-32, Neuroscience Inc, Tokyo, Japan) under fasting and water-deprivation. The locomotor activities in the former half (6 hr) of the dark phase were measured and the data was collected by a multidigital counter (Neuroscience Inc, Tokyo, Japan).

Figure 3B:
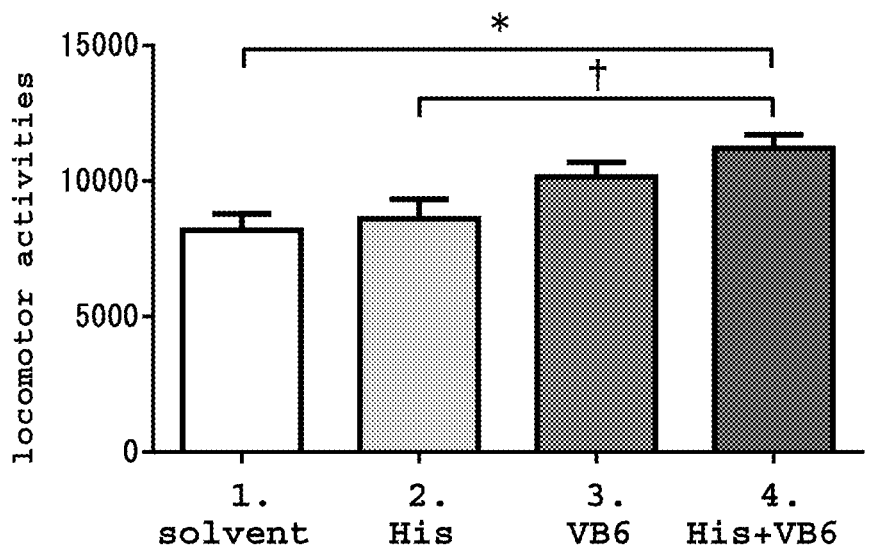
FIG. 3B shows cumulative locomotor activities for the former half (6 hr) of the dark phase when histidine (His) and/or vitamin B6 (VB6) are used. *: Tukey's multiple test, $p<0.05$. †: Tukey's multiple test, $p<0.1$.

The results are shown in FIG. 3B. In the combined use group to which His and vitamin B6 (VB6) were given for one week, locomotor activities were significantly improved in the former half of the dark phase as compared to the solvent group, and the locomotor activities tended to improve as compared to the His ingestion group, it was clarified that the combined use of His and vitamin B6 shows an anti-fatigue effect.

Figure 3C:
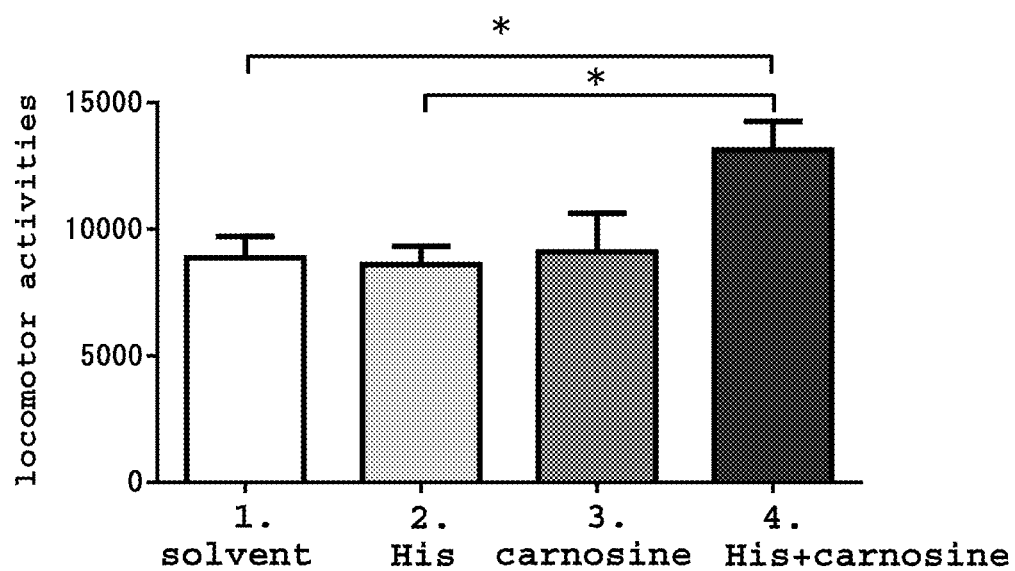
FIG. 3C shows cumulative locomotor activities for the former half (6 hr) of the dark phase when histidine (His) and/or carnosine are used. *: Tukey's multiple test, $p<0.05$.

The combined use with carnosine was also examined in the same manner. The results are shown in FIG. 3C. It was clarified that the combined use of His and carnosine also shows an anti-fatigue effect. On the other hand, other materials (7 materials) shown in Table 3 did not show an anti-fatigue effect whether each material was used alone or in combination with His.

TABLE 3

| | | anti-fatigue effect | | |
|---|---|---|---|---|
| test substance X | ingestion amount (mg/kg/day) | 2. His | 3. test substance X | 4. combined use |
| vitamin B12 | 6 | x | x | x |
| vitamin B1 | 50 | x | x | x |
| vitamin B6 | 300 | x | x | ○ |
| DHA | 700 | x | x | x |
| zinc | 30 | x | x | x |
| creatine | 400 | x | x | x |
| L-carnitine | 500 | x | x | x |
| α-glycerophosphocholine | 600 | x | x | x |
| carnosine | 1800 | x | x | ○ |

From the above results, it was clarified that a composition containing histidine and vitamin B6 or carnosine has an anti-fatigue effect.

Figure 4A:
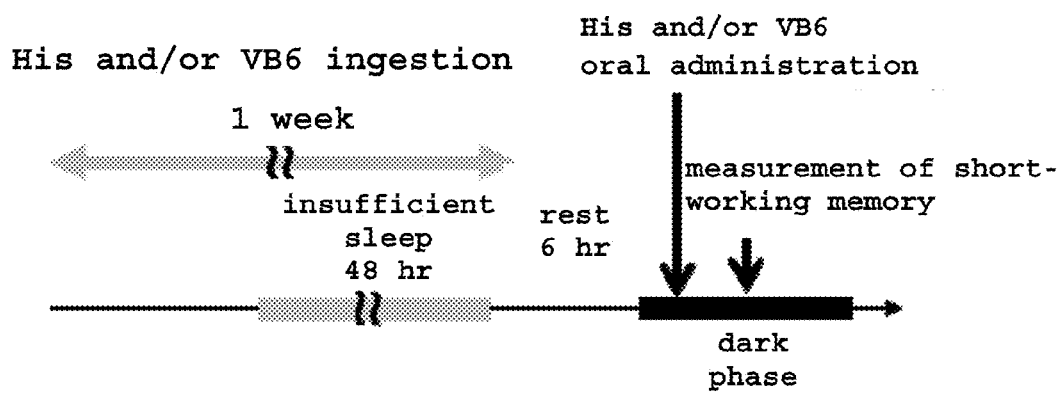
FIG. 4A shows the protocol for verifying the effect of the ingestion of histidine (His) and/or vitamin B6 (VB6) on the change of short-working memory (fatigue index) of mouse after burden of insufficient sleep.

Example 2: Verification of Effect of Ingestion of the Present Invention (his:VB6=30:1) on Decrease in Short-Working Memory (Index of Fatigue) after Burden of Insufficient Sleep Using CD2F1 mice (9-10-week-old) in the group constitution shown in Table 4, the test was performed as shown in the experiment protocol (FIG. 4A).

TABLE 4

| group | | free drinking ingestion amount (mg/kg/day) | | dose (mg/kg) | |
|---|---|---|---|---|---|
| No. | group name | His | VB6 | His | VB6 |
| 1. | solvent group | — | — | — | — |
| 2. | His group | 900 | — | 900 | — |
| 3. | VB6 group | — | 30 | — | 30 |
| 4. | His + VB6 group | 900 | 30 | 900 | 30 |

The His group and His+VB6 group were allowed to drink each solution freely for one week so that the ingestion amount of His would be 900 mg/kg/day, and the ingestion amount of the VB6 group and the His+VB6 group would be 30 mg/kg/day. As the feed, a feed having the composition of Table 5 was used.

TABLE 5

| component | (%) |
|---|---|
| feed composition | |
| amino acid mix | 20.0000 |
| L-cystine | 0.3000 |
| cornstarch | 39.7486 |
| pregelatinized cornstarch | 13.2000 |
| sucrose | 10.0000 |
| soybean oil | 7.0000 |
| cellulose powder | 5.0000 |
| AIN-93G mineral mix | 3.5000 |
| AIN-93G vitamin mix | 1.0000 |

TABLE 5-continued

| component | (%) |
|---|---|
| choline bitartrate | 0.2500 |
| tertiary butylhydroquinone | 0.0014 |
| composition of amino acid mix | |
| Ala | 2.25 |
| Arg | 3.28 |
| Asn-H2O | 3.60 |
| Asp | 3.16 |
| Cys-Cys | 0.50 |
| Gln | 12.04 |
| Glu | 9.16 |
| Gly | 1.62 |
| His | 0.51 |
| Ile | 4.45 |
| Leu | 8.13 |
| Lys-HCl | 8.82 |
| Met | 2.43 |
| Phe | 4.50 |
| Pro | 9.37 |
| Ser | 5.06 |
| Thr | 3.81 |
| Trp | 1.08 |
| Tyr | 4.85 |
| Val | 5.73 |
| Starch | 5.34 |

After ingestion of His or VB6, or both for one week, insufficient sleep was burdened for 48 hr by filling water in the breeding cage at the depth of 0.5 cm. The burden was released at 6 hr from the start of the light phase, and the mice were placed back in the home cage and allowed to rest for 6 hr. Thereafter, the His group and His+VB6 group were orally administered with His, and the VB6 group and His+VB6 group were orally administered with VB6 at 2 hr from the start of the dark phase after burden of insufficient sleep to achieve the doses in Table 4. A Y-maze test was performed at 3 hr from the start of the dark phase, and short-working memory was measured.

Figure 4B:
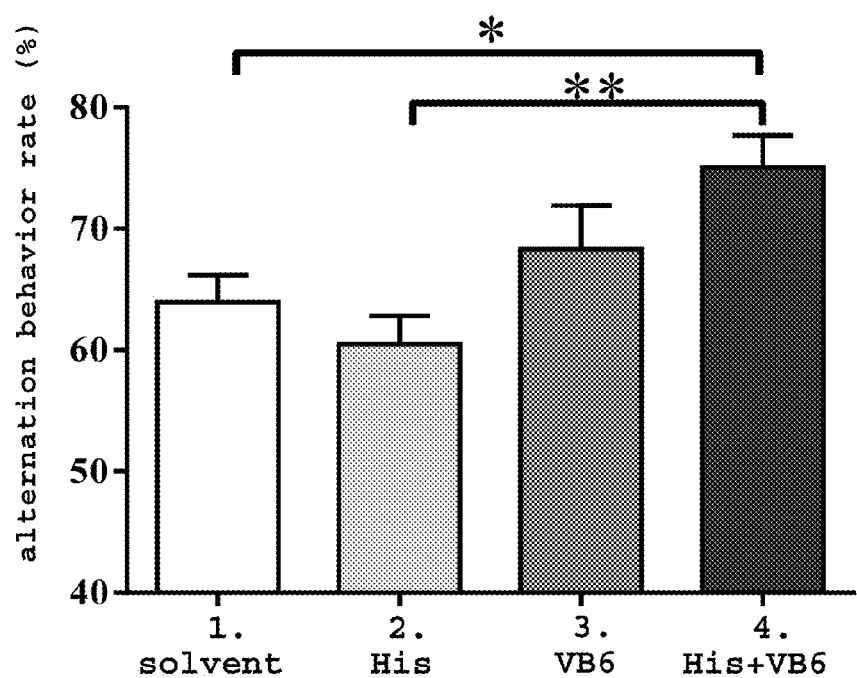
FIG. 4B shows the measurement results of alternation behavior. **: Tukey's multiple test, p<0.01. *: Tukey's multiple test, p<0.05.

The results are shown in FIG. 4B. After burden of insufficient sleep that induces fatigue, the His+VB6 group showed a significant increase in the alternation behavior as compared to the solvent group or His group.

From the above results, it was clarified that the composition of the present invention containing His:VB6=30:1 has an anti-fatigue effect.

Figure 5A:
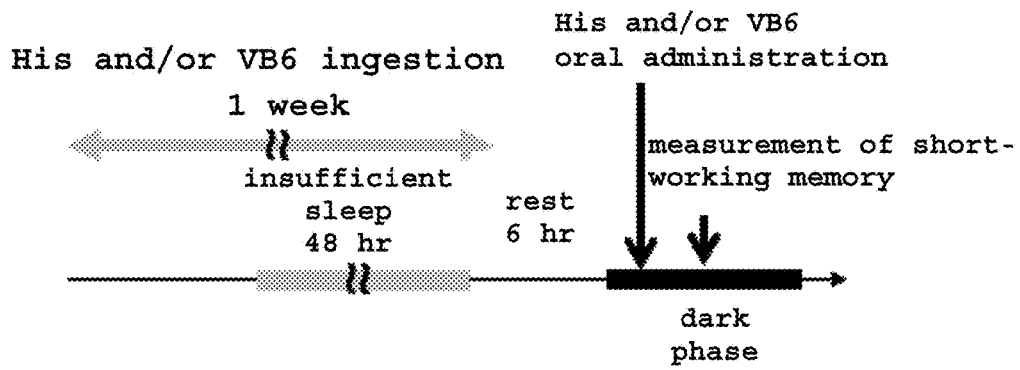
FIG. 5A shows the protocol for verifying the effect of the ingestion of histidine (His) and/or vitamin B6 (VB6) (His: VB6=120:1) on the change of short-working memory (fatigue index) of mouse after burden of insufficient sleep.

Example 3: Verification of Effect of Ingestion of the Present Invention (his:VB6=120:1) on Decrease in Short-Working Memory (Index of Fatigue) after Burden of Insufficient Sleep Using CD2F1 mice (9-10-week-old) in the group constitution shown in Table 6, the test was performed as shown in the experiment protocol (FIG. 5A).

TABLE 6

| group | | free drinking ingestion amount (mg/kg/day) | | dose (mg/kg) | |
|---|---|---|---|---|---|
| No. | group name | His | VB6 | His | VB6 |
| 1. | solvent group | — | — | — | — |
| 2. | His group | 900 | — | 900 | — |
| 3. | VB6 group | — | 7.5 | — | 7.5 |
| 4. | His + VB6 group | 900 | 7.5 | 900 | 7.5 |

The His group and His+VB6 group were allowed to drink each solution freely for one week so that the ingestion amount of His would be 900 mg/kg/day, and the ingestion amount of the VB6 group and the His+VB6 group would be 7.5 mg/kg/day. As the feed, a feed having the composition of Table 5 was used.

After ingestion of His or VB6, or both for one week, insufficient sleep was burdened for 48 hr by filling water in the breeding cage at the depth of 0.5 cm. The burden was released at 6 hr from the start of the light phase, and the mice were placed back in the home cage and allowed to rest for 6 hr. Thereafter, the His group and His+VB6 group were orally administered with His, and the VB6 group and His+VB6 group were orally administered with VB6 at 2 hr from the start of the dark phase after burden of insufficient sleep to achieve the doses in Table 6. A Y-maze test was performed at 3 hr from the start of the dark phase, and short-working memory was measured.

Figure 5B:
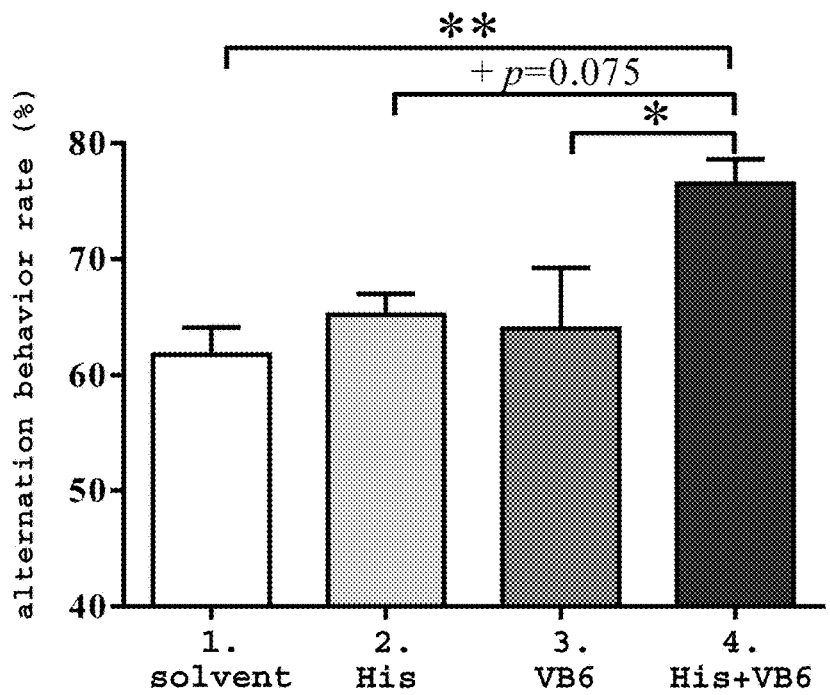
FIG. 5B shows the measurement results of alternation behavior. **: Tukey's multiple test, p<0.01. *: Tukey's multiple test, p<0.05.

The results are shown in FIG. 5B. After burden of insufficient sleep that induces fatigue, the His+VB6 group showed a significant increase in the alternation behavior as compared to the solvent group or VB6 group, and an increase tendency in the alternation behavior as compared to the His group.

Figure 6A:
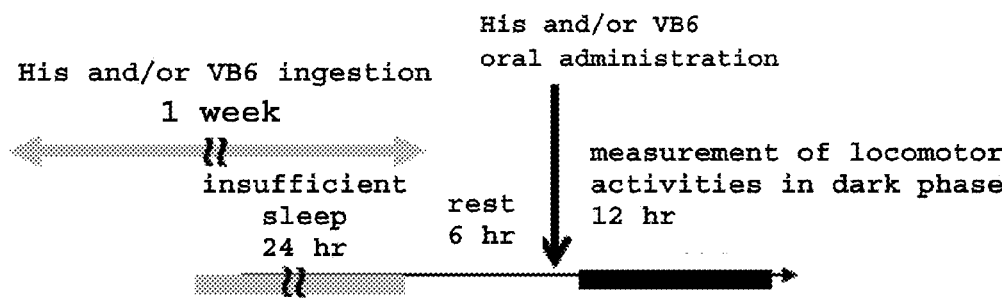
FIG. 6A shows the protocol for verifying the effect of the ingestion of histidine (His) and/or vitamin B6 (VB6) (His: VB6=120:1) on the change of locomotor activities (fatigue index) of mouse after burden of insufficient sleep.

Example 4: Verification of Effect of Ingestion of the Present Invention (his:VB6=120:1) on Locomotor Activities in the Dark Phase (Index of Fatigue) after Burden of Insufficient Sleep Using CD2F1 mice (9-10-week-old) in the group constitution shown in Table 6, the test was performed as shown in the experiment protocol (FIG. 6A).

The His group and His+VB6 group were allowed to drink each solution freely for one week so that the ingestion amount of His would be 900 mg/kg/day, and the ingestion amount of the VB6 group and the His+VB6 group would be 7.5 mg/kg/day. As the feed, a feed having the composition of Table 5 was used.

After ingestion of His or VB6, or both for one week, insufficient sleep was burdened for 24 hr by filling water in the breeding cage at the depth of 0.5 cm. The burden was released at 6 hr from the start of the light phase, and the mice were placed back in the home cage and allowed to rest for 6 hr. Thereafter, the His group and His+VB6 group were orally administered with His, and the VB6 group and His+VB6 group were orally administered with VB6 at 1 hr before the start of the dark phase to achieve the doses in Table 6. The locomotor activities in the dark phase were measured by a multidigital counter (Neuroscience Inc., Tokyo, Japan).

Figure 6B:
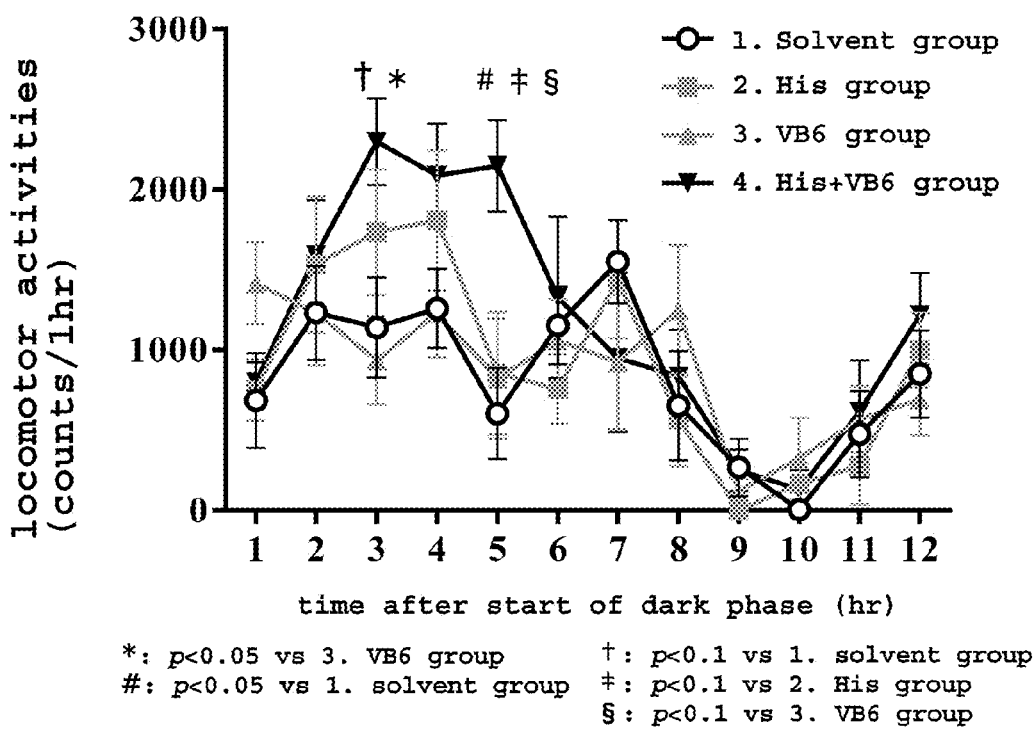
FIG. 6B shows the measurement results of locomotor activities in the dark phase. *: Tukey's multiple test, p<0.05 vs VB6 group. #: Tukey's multiple test, p<0.05 vs solvent group. †: Tukey's multiple test, p<0.1 vs solvent group. ‡: Tukey's multiple test, p<0.1 vs His group. §: Tukey's multiple test, p<0.1 vs VB6 group.
Figure 6C:
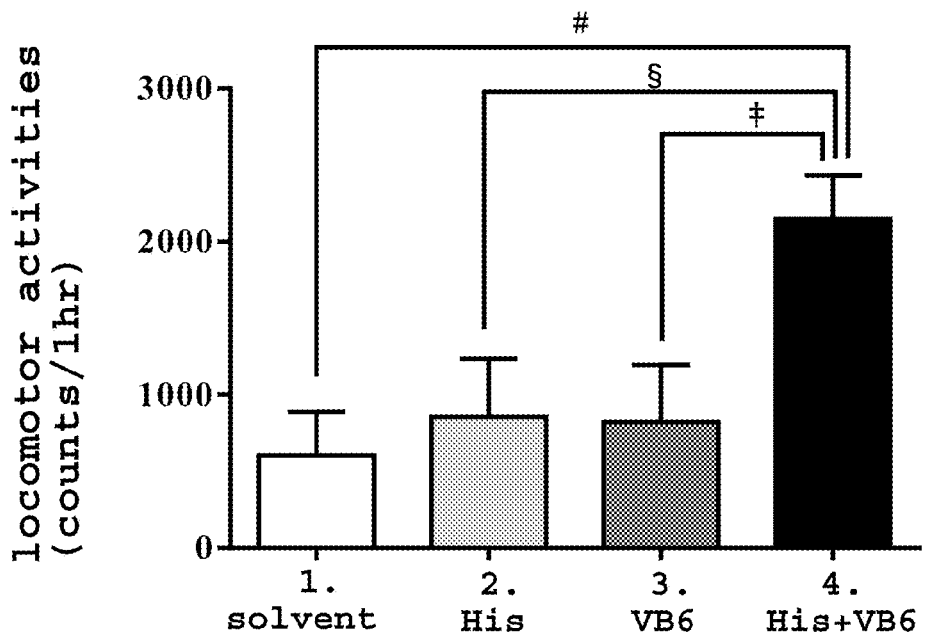
FIG. 6C shows the measurement results of locomotor activities in 4 hr to 5 hr after the start of the dark phase. #: Tukey's multiple test, p<0.05 vs solvent group. ‡: Tukey's multiple test, p<0.1 vs His group. §: Tukey's multiple test, p<0.1 vs VB6 group.

The results are shown in FIG. 6B and FIG. 6C. At 4-5 hr after the start of the dark phase, the His+VB6 group showed a significant increase as compared to the solvent group, and an increase tendency as compared to the His group and the VB6 group.

From the results of Example 3 and Example 4, it was clarified that the composition of the present invention containing His:VB6=120:1 has an anti-fatigue effect.

Figure 7A:
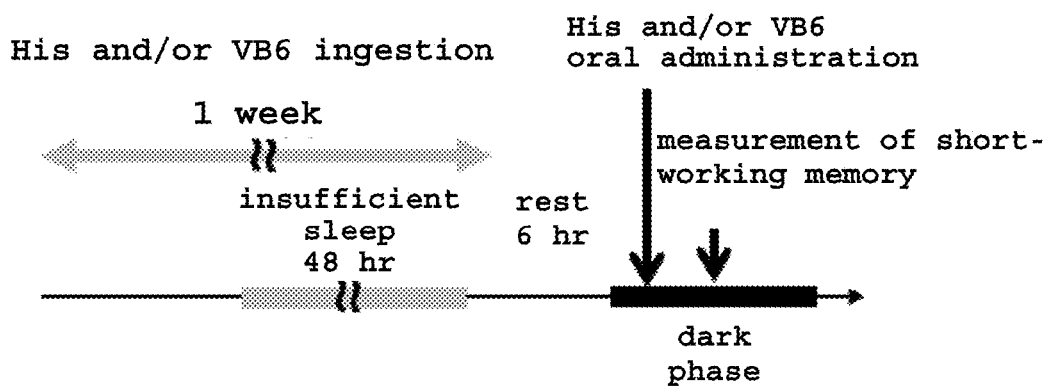
FIG. 7A shows the protocol for verifying the effect of the ingestion of histidine (His) and/or vitamin B6 (VB6) (His: VB6=360:1) on the change of short-working memory (fatigue index) of mouse after burden of insufficient sleep.

Example 5: Verification of Effect of Ingestion of the Present Invention (his:VB6=360:1) on Decrease in Short-Working Memory (Index of Fatigue) after Burden of Insufficient Sleep Using CD2F1 mice (10-21-week-old) in the group constitution shown in Table 7, the test was performed as shown in the experiment protocol (FIG. 7A).

TABLE 7

| group No. | group name | free drinking ingestion amount (mg/kg/day) His | free drinking ingestion amount (mg/kg/day) VB6 | dose (mg/kg) His | dose (mg/kg) VB6 |
|---|---|---|---|---|---|
| 1. | solvent group | — | — | — | — |
| 2. | His group | 900 | — | 900 | — |
| 3. | VB6 group | — | 2.5 | — | 2.5 |
| 4. | His + VB6 group | 900 | 2.5 | 900 | 2.5 |

The His group and His+VB6 group were allowed to drink each solution freely for one week so that the ingestion amount of His would be 900 mg/kg/day, and the ingestion amount of the VB6 group and the His+VB6 group would be 2.5 mg/kg/day. As the feed, a feed having the composition of Table 5 was used.

After ingestion of His or VB6, or both for one week, insufficient sleep was burdened for 48 hr by filling water in the breeding cage at the depth of 0.5 cm. The burden was released at 6 hr from the start of the light phase, and the mice were placed back in the home cage and allowed to rest for 6 hr. Thereafter, the His group and His+VB6 group were orally administered with His, and the VB6 group and His+VB6 group were orally administered with VB6 at 2 hr after the start of the dark phase after burden of insufficient sleep to achieve the doses in Table 7. A Y-maze test was performed at 3 hr from the start of the dark phase, and short-working memory was measured.

Figure 7B:
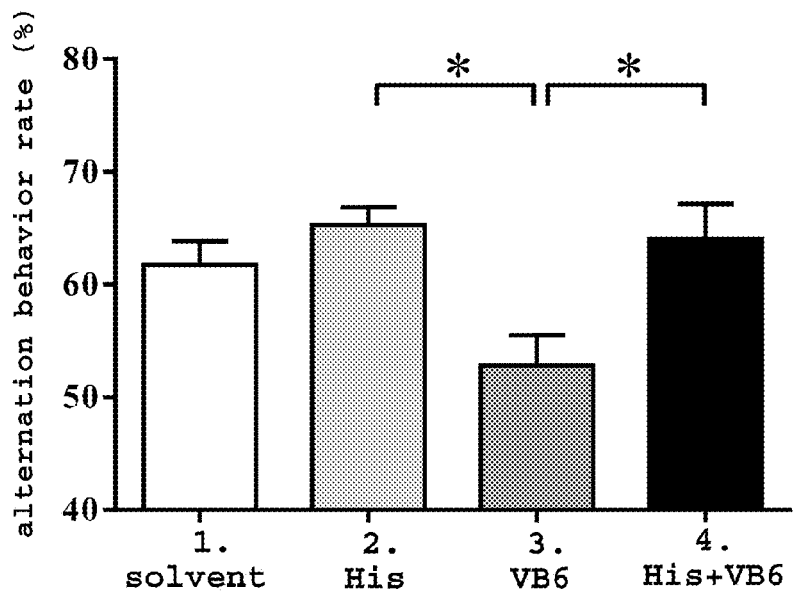
FIG. 7B shows the measurement results of alternation behavior. *: Tukey's multiple test, p<0.05.

The results are shown in FIG. 7B. After burden of insufficient sleep that induces fatigue, the His+VB6 group and His group showed a significant increase in the alternation behavior as compared to the VB6 group, but no group showed a significant increase as compared to the solvent group.

Figure 8A:
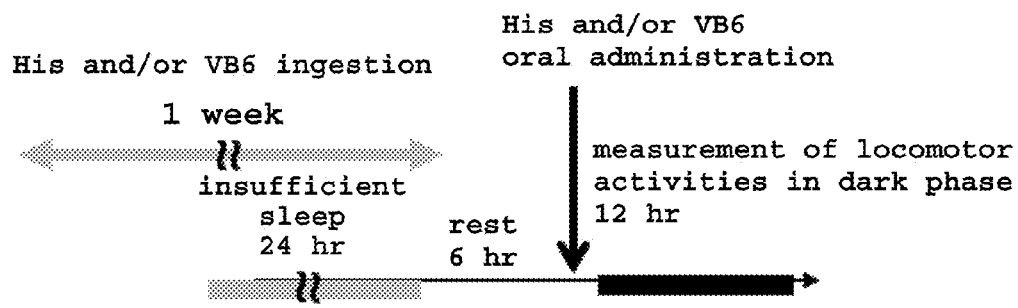
FIG. 8A shows the protocol for verifying the effect of the ingestion of histidine (His) and/or vitamin B6 (VB6) (His: VB6=360:1) on the change of locomotor activities (fatigue index) of mouse after burden of insufficient sleep.

Example 6: Verification of Effect of Ingestion of the Present Invention (his:VB6=360:1) on Locomotor Activities in the Dark Phase (Index of Fatigue) after Burden of Insufficient Sleep Using CD2F1 mice (10-11-week-old) in the group constitution shown in Table 7, the test was performed as shown in the experiment protocol (FIG. 8A).

The His group and His+VB6 group were allowed to drink each solution freely for one week so that the ingestion amount of His would be 900 mg/kg/day, and the ingestion amount of the VB6 group and the His+VB6 group would be 2.5 mg/kg/day. As the feed, a feed having the composition of Table 5 was used.

After ingestion of His or VB6, or both for one week, insufficient sleep was burdened for 24 hr by filling water in the breeding cage at the depth of 0.5 cm. The burden was released at 6 hr from the start of the light phase, and the mice were placed back in the home cage and allowed to rest for 6 hr. Thereafter, the His group and His+VB6 group were orally administered with His, and the VB6 group and His+VB6 group were orally administered with VB6 at 1 hr before the start of the dark phase to achieve the doses in Table 7. The locomotor activities in the dark phase were measured by a multidigital counter (Neuroscience Inc., Tokyo, Japan).

Figure 8B:
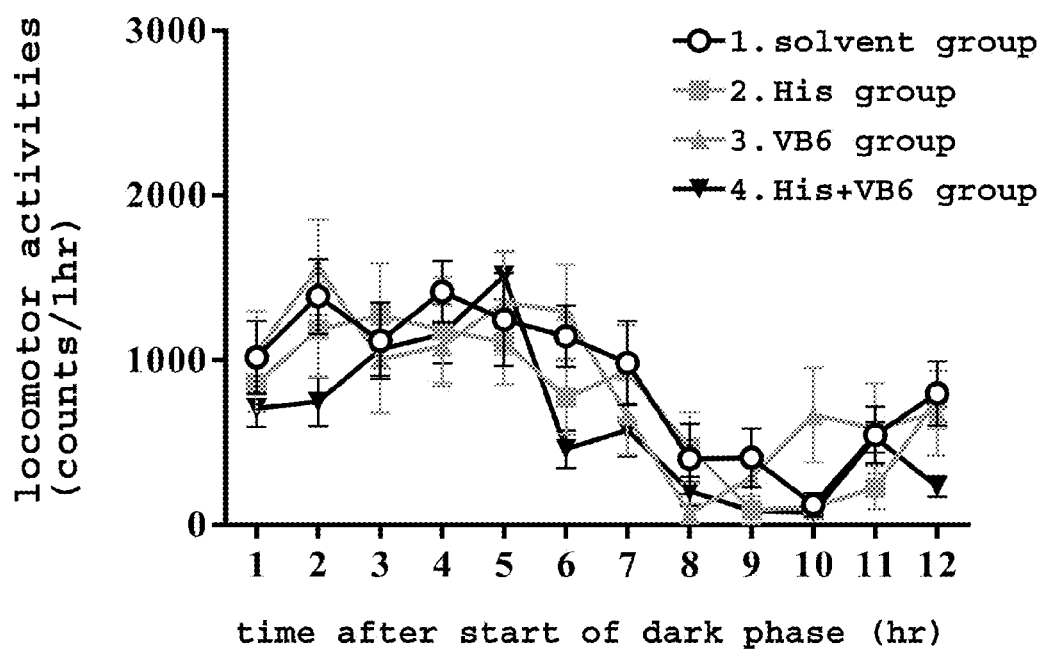
FIG. 8B shows the measurement results of locomotor activities in the dark phase.

The results are shown in FIG. 8B. No group showed a significant increase in the activities as compared to the solvent group.

Figure 11A:
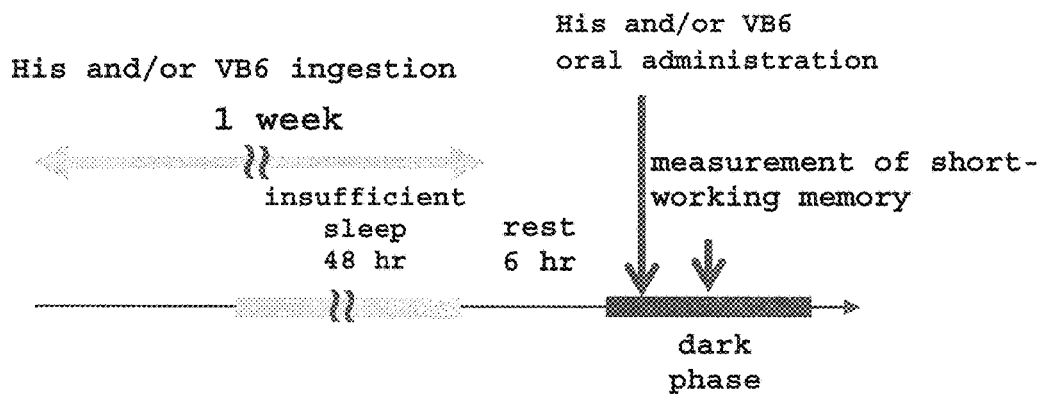
FIG. 11A shows the protocol for verifying the effect of the ingestion of histidine (His) and/or vitamin B6 (VB6) (His: VB6=300:1) on the change of short-working memory (fatigue index) of mouse after burden of insufficient sleep.

Example 7: Verification of Effect of Ingestion of the Present Invention (his:VB6=300:1) on Decrease in Short-Working Memory (Index of Fatigue) after Burden of Insufficient Sleep Using CD2F1 mice (10-21-week-old) in the group constitution shown in Table 8, the test was performed as shown in the experiment protocol (FIG. 11A).

TABLE 8

| group No. | group name | free drinking ingestion amount (mg/kg/day) His | free drinking ingestion amount (mg/kg/day) VB6 | dose (mg/kg) His | dose (mg/kg) VB6 |
|---|---|---|---|---|---|
| 1. | solvent group | — | — | — | — |
| 2. | His group | 900 | — | 900 | — |
| 3. | VB6 group | — | 3.0 | — | 3.0 |
| 4. | His + VB6 group | 900 | 3.0 | 900 | 3.0 |

The His group and His+VB6 group were allowed to drink each solution freely for one week so that the ingestion amount of His would be 900 mg/kg/day, and the ingestion amount of the VB6 group and the His+VB6 group would be 3.0 mg/kg/day. As the feed, a feed having the composition of Table 5 was used.

After ingestion of His or VB6, or both for one week, insufficient sleep was burdened for 48 hr by filling water in the breeding cage at the depth of 0.5 cm. The burden was released at 6 hr from the start of the light phase, and the mice were placed back in the home cage and allowed to rest for 6 hr. Thereafter, the His group and His+VB6 group were orally administered with His, and the VB6 group and His+VB6 group were orally administered with VB6 at 2 hr from the start of the dark phase after burden of insufficient sleep to achieve the doses in Table 8. A Y-maze test was performed at 3 hr from the start of the dark phase, and short-working memory was measured.

Figure 11B:
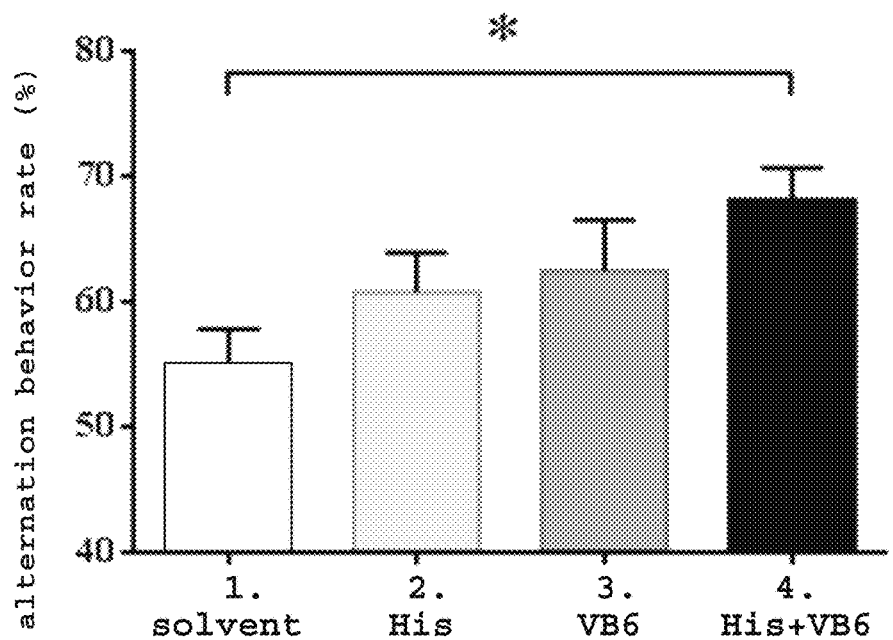
FIG. 11B shows the measurement results of alternation behavior. *: Tukey's multiple test, p<0.05.

The results are shown in FIG. 11B. After burden of insufficient sleep that induces fatigue, the His+VB6 group showed a significant increase in the alternation behavior as compared to the solvent group.

Formulation Example 1 Histidine and Vitamin B6-Containing Tablet

A histidine and vitamin B6-containing tablet having the following combination is produced by tableting according to a conventional method. The tablet weight is 340 mg.

TABLE 9

| each component | combination ratio (%) |
|---|---|
| L-histidine | 76.048 |
| starch syrup of reduced malt sugar | 11.812 |
| cellulose | 9.506 |
| calcium stearate | 2 |
| vitamin B6 | 0.634 |
| total | 100 |

Formulation Example 2 Histidine and Vitamin B6-Containing Solution

A histidine and vitamin B6-containing solution having the following combination is produced by a conventional method. The solution weight is 30 g.

TABLE 10

| each component | combination ratio (%) |
|---|---|
| L-histidine | 5.333 |
| vitamin B6 | 0.050 |
| sweetener | 4.000 |
| erythritol | 10.000 |
| high-intensity sweetener | 0.013 |
| citric acid | 4.000 |
| flavor | 0.060 |
| water | 76.544 |
| total | 100.000 |

Formulation Example 3 Histidine and Vitamin B6-Containing Granules

Histidine and vitamin B6-containing granules having the following combination are produced by a conventional method. The volume is 2 g.

TABLE 11

| each component | combination ratio (%) |
|---|---|
| L-histidine | 80.000 |
| vitamin B6 | 0.700 |
| excipient | 10.980 |
| high-intensity sweetener | 0.420 |
| citric acid | 6.400 |
| flavor | 1.500 |
| total | 100.000 |

Formulation Example 4 Histidine and Vitamin B6-Containing Jelly

A histidine and vitamin B6-containing jelly having the following combination is produced by a conventional method. The weight is 100 g.

TABLE 12

| each component | combination ratio (%) |
|---|---|
| L-histidine | 1.600 |
| vitamin B6 | 0.015 |
| gellant | 0.800 |
| fruit juice | 0.265 |
| sweetener | 2.500 |
| high-intensity sweetener | 0.023 |
| citric acid | 1.861 |
| flavor | 0.200 |
| water | 92.736 |

Reference Example 1 Verification of Effect of Histidine (His) Ingestion for 14 Days in Males Feeling Decrease in the Quality of Sleep and Fatigue Twenty males of 45 years old to less than 65 years old, who received total evaluation of not less than 17 points in the "self-diagnosis fatigue questionnaire" (Fatigue Science Laboratory Inc.), felt decrease in the quality of sleep (generally PSQI≥6), and obtained fatigue factor T scores of not less than 60 points in POMS, performed in advance, were selected, and randomly divided into 2 groups (10 per group). A crossover test, including ingesting histidine and control food (equal volume of cellulose) each for 14 days, was performed in each group.

Figure 9A:
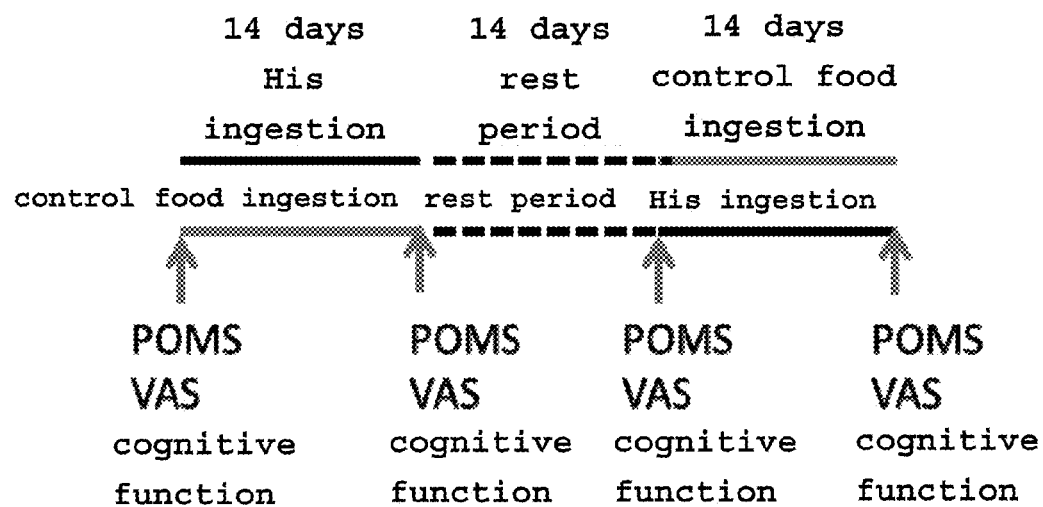
FIG. 9A shows the protocol for verifying the anti-fatigue effect of histidine (His) ingestion in test subjects feeling fatigue and a decrease in the quality of sleep.
Figure 9B:
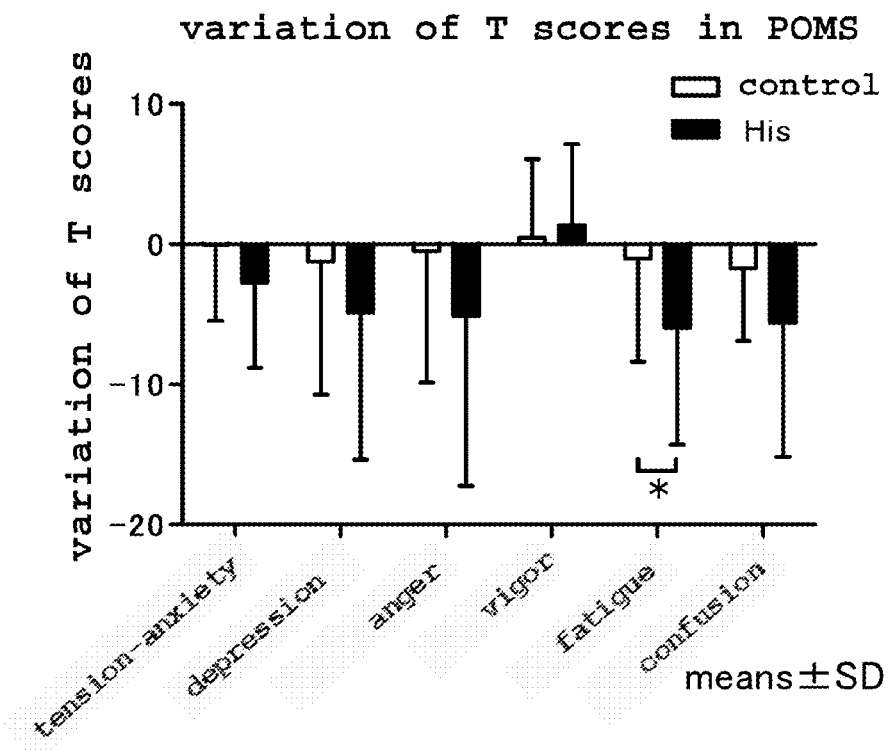
FIG. 9B shows variation of T scores in POMS. *: paired t-test, p<0.05.

As shown in the experiment protocol of FIG. 9A, the test subjects ingested capsules containing 1.65 g of L-histidine as a daily ingestion amount (5 capsules (hard capsule #2 WHITE OP B/C) containing 0.33 g of L-histidine alone), or control sample capsules (5 capsules containing equal volume of cellulose) for 14 days. After the completion of 14 day ingestion, a 14 day resting period was taken. After the resting period, they ingested the capsules not ingested before the resting period.

On the initial day and the day after completion of the capsule ingestion period, the test subjects answered POMS and the VAS questionnaires (fatigue, depression, vague sense, drowsiness, clear thinking, motivation, attentiveness, concentration) relating to fatigue, and cognitive function measurement task CogHealth (under higher difficulty conditions by simultaneously including mental arithmetic task as well) to measure intellectual performance which is one of the fatigue indices. Furthermore, they answered VAS questionnaires after completion of CogHealth. Evaluation after completion of CogHealth reveals the difference of the state between after and before the work-load.

Figure 9D:
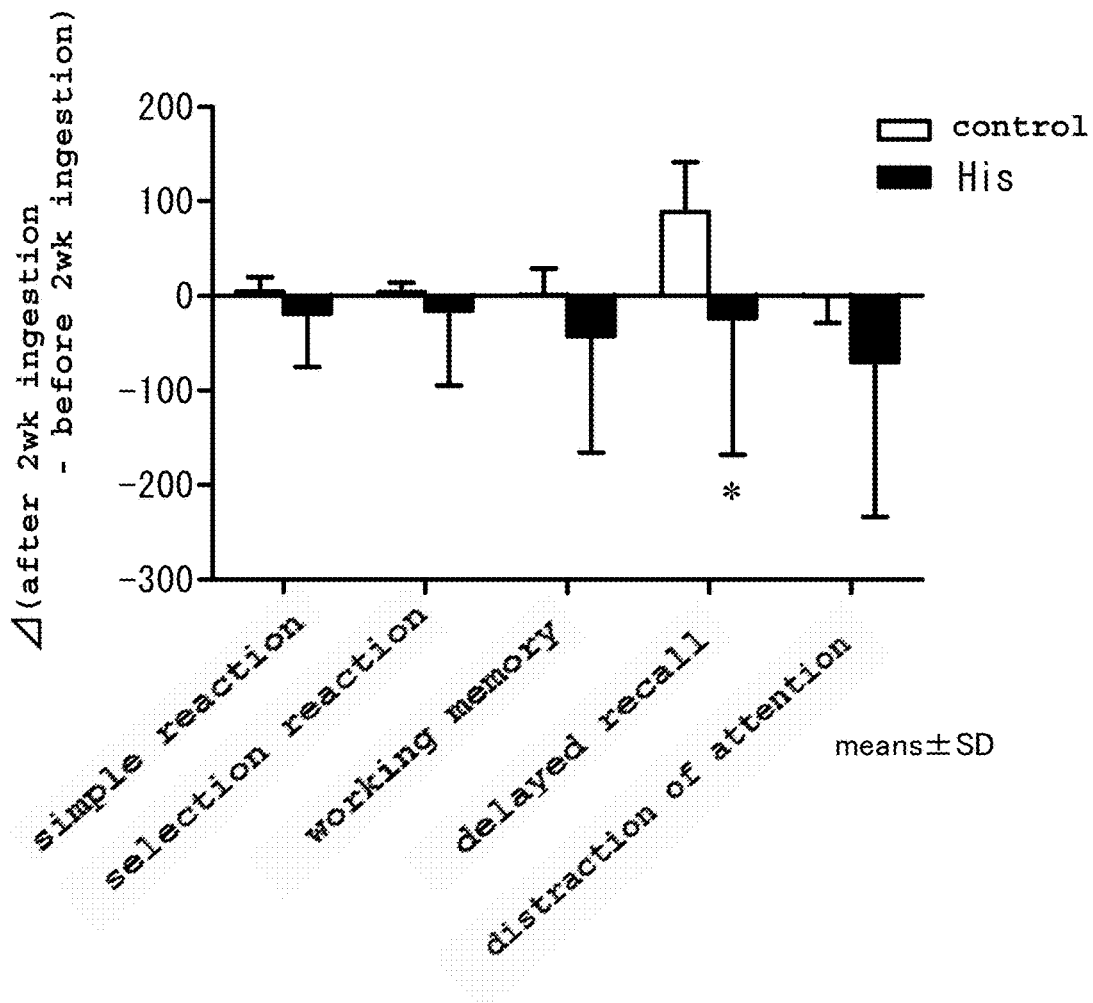
FIG. 9D shows variation in the reaction time in cognitive functioning test. *: paired t-test, p<0.05.
Figure 9E:
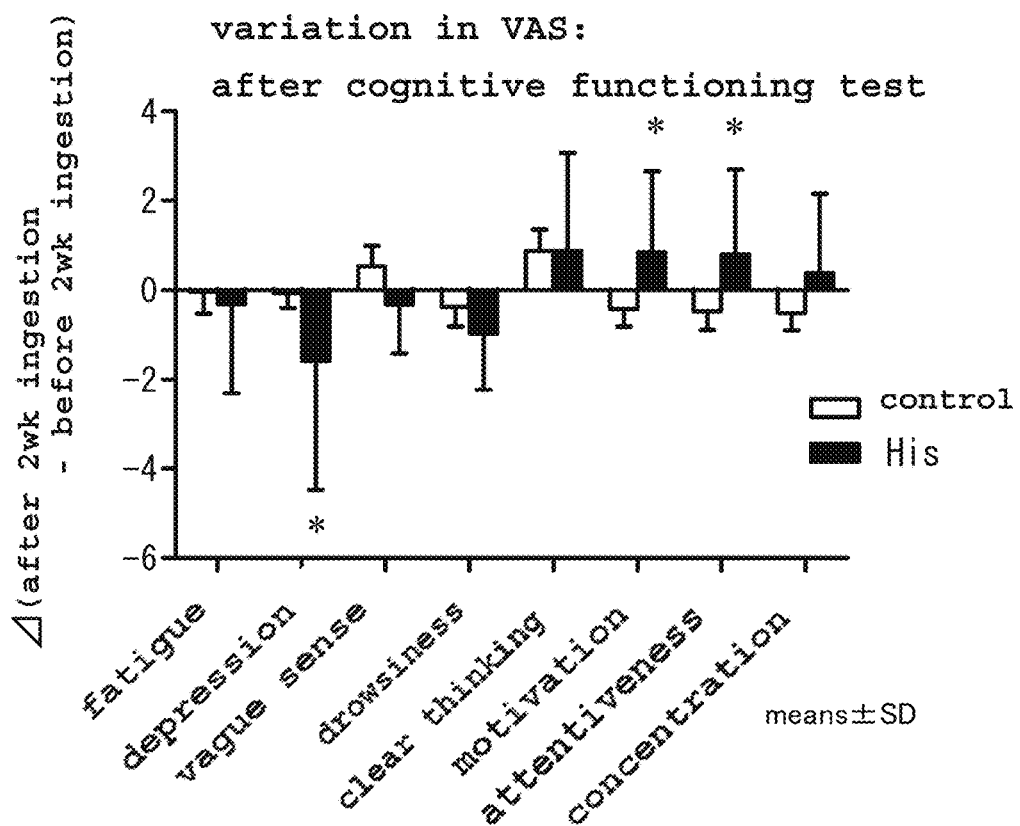
FIG. 9E shows variation of each index in VAS after cognitive functioning test. *: paired t-test, p<0.05.

The results are shown in FIGS. 9B to 9E. As compared to the test subjects who ingested the control food, the fatigue factor scores of POMS significantly decreased (paired t-test: $p<0.05$) (FIG. 9B) and the sense of clear thinking, motivation, and attentiveness significantly increased (paired t-test: $p<0.05$) in VAS questionnaires relating to fatigue (FIG. 9C) in the test subjects who ingested histidine for 14 days. In the intellectual work efficiency, ingestion of histidine shortened the reaction time of cognitive function measurement task and significantly decreased the reaction time of delayed recall task (paired t-test: $p<0.05$) as compared to ingestion of the control food (FIG. 9D). In VAS questionnaires after completion of CogHealth, moreover, the sense of depression significantly decreased and the sense of motivation and attentiveness significantly increased (paired t-test: $p<0.05$) (FIG. 9E). This means that an increase in motivation and attentiveness can be maintained, and feeling of depression by burden can be suppressed, even when cognitive work is loaded.

From the above results, it was clarified that an agent containing histidine can improve/recover fatigue.

Reference Example 2 Verification of Effect of Single Histidine (his) Ingestion in Males Feeling Decrease in the Quality of Sleep and Fatigue Twenty males of 45 years old to less than 65 years old, who received total evaluation of not less than 17 points in the "self-diagnosis fatigue questionnaire" (Fatigue Science Laboratory Inc.), felt decrease in the quality of sleep (generally PSQI≥6), and obtained fatigue factor T scores of not less than 60 points in POMS performed in advance, were selected, and randomly divided into 2 groups (10 per group). The effect of single ingestion of histidine and control food (equal volume of cellulose) was compared in each group.

Figure 10A:
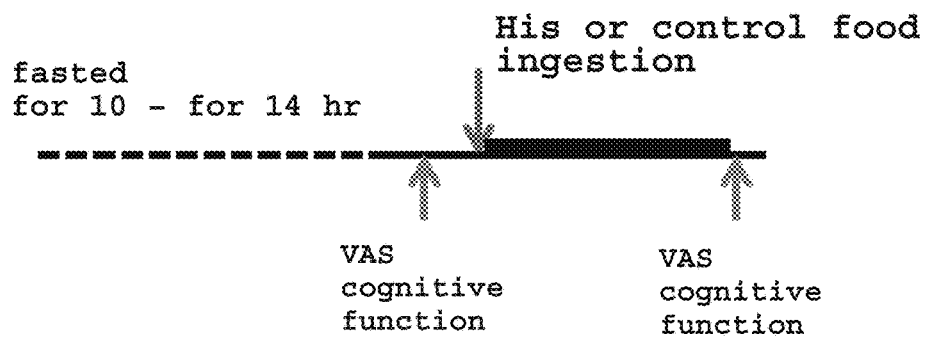
FIG. 10A shows the protocol for verifying the anti-fatigue effect of single histidine (His) ingestion in test subjects feeling fatigue and a decrease in the quality of sleep.

As shown in the experiment protocol of FIG. 10A, the test subjects took the same meals for 3 days before the experiment, fasted for 10 to for 14 hr, and ingested capsules containing 1.65 g of L-histidine as a single ingestion amount (5 capsules (hard capsule #2 WHITE OP B/C) containing 0.33 g of L-histidine alone), or control sample capsules (5 capsules containing equal volume of cellulose).

Before and 1 hr after ingestion of capsules, the test subjects answered the VAS questionnaires (fatigue, depression, vague sense, drowsiness, clear thinking, motivation, attentiveness, concentration) relating to fatigue, and cognitive function measurement task CogHealth (under higher difficulty conditions by simultaneously including mental arithmetic task as well) to measure intellectual performance which is one of the fatigue indices. Furthermore, they answered VAS questionnaires after completion of CogHealth. Evaluation after completion of CogHealth reveals the difference of the state between after and before the work-load.

Figure 10B:
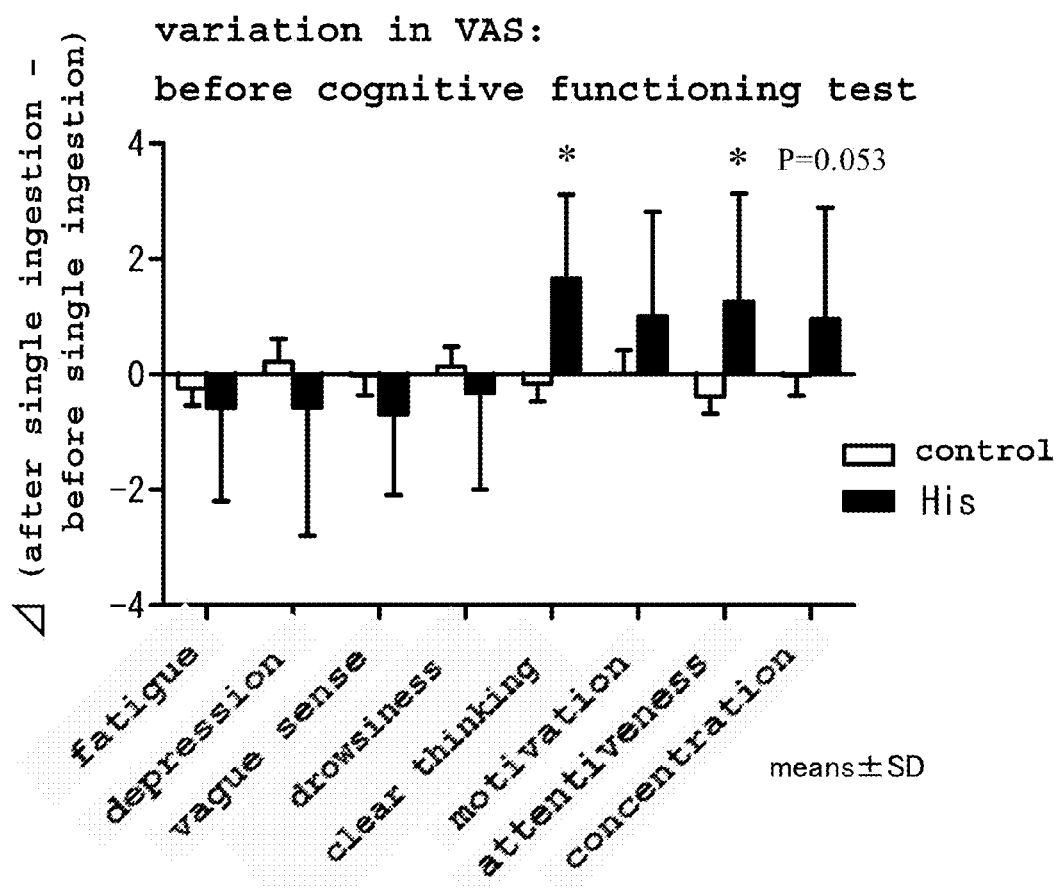
FIG. 10B shows variation of each index in VAS before cognitive functioning test (CogHealth). *: paired t-test, p<0.05.
Figure 10C:
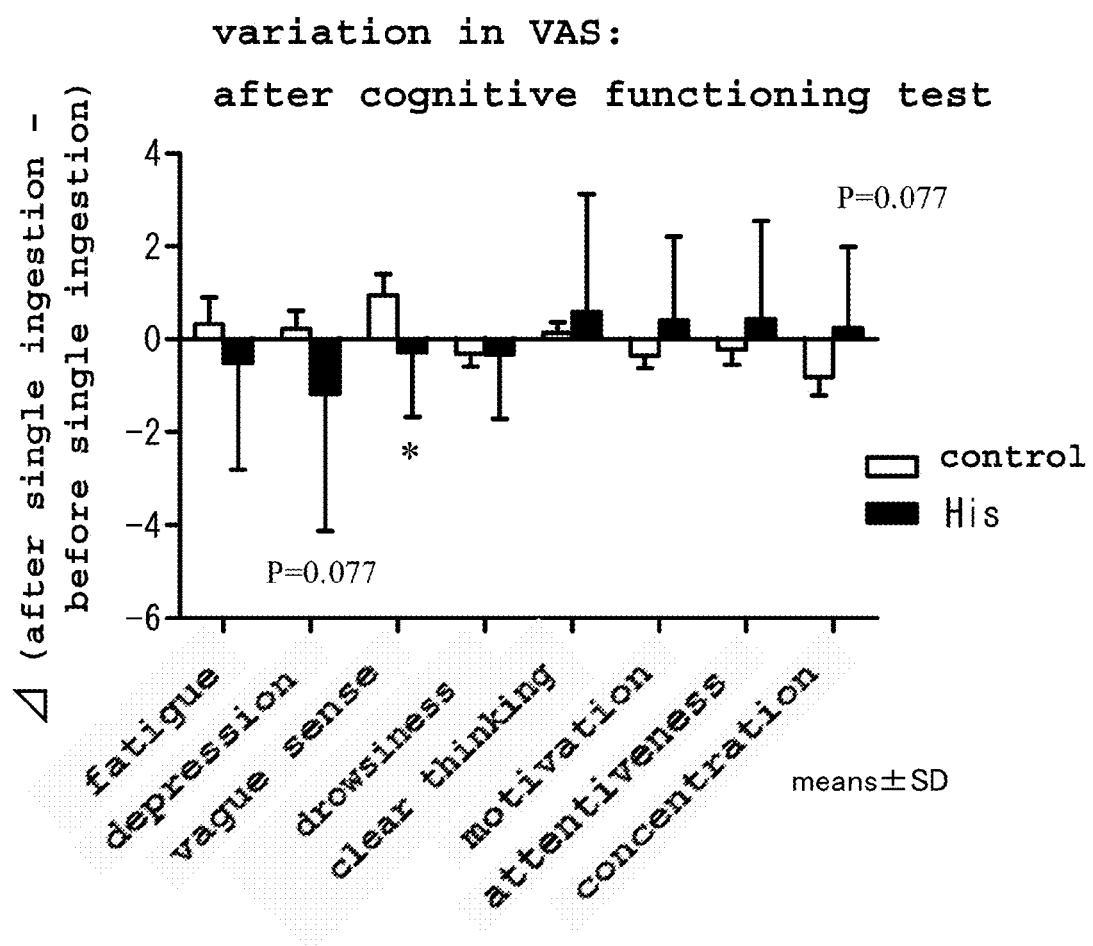
FIG. 10C shows variation of each index in VAS after cognitive functioning test. *: paired t-test, p<0.05.

The results are shown in FIGS. 10B and 10C. It was found that the work time in 5 kinds of brain function measurement indices was shortened in the test subjects who ingested histidine, as compared to the test subjects who ingested the control food. In VAS questionnaires relating to fatigue, the sense of clear thinking and attentiveness significantly increased and the sense of concentration tended to increase (paired t-test: $p<0.05$) (FIG. 10B). In VAS questionnaires after completion of CogHealth, moreover, the sense of vague sense significantly decreased, the sense of depression tended to decrease, and the sense of concentration tended to increase (paired t-test: $p<0.05$) (FIG. 10O). This means that ingestion of histidine may be able to suppress vague sense and the sense of depression due to burden and maintain concentration, even when cognitive work is loaded.

From the above results, it was clarified that an agent containing histidine can improve/recover fatigue.

As mentioned above, continuous ingestion of histidine for 2 weeks showed improvement/recovery of fatigue, and a single ingestion of His showed improvement/recovery of fatigue. Ingestion of His did not show problematic variation in general properties, hematology, and blood biochemistry from the aspects of safety.

INDUSTRIAL APPLICABILITY

Fatigue (mental fatigue, physical fatigue) can be improved by ingesting the composition of the present invention comprising (1) histidine and (2) vitamin B6 and/or carnosine. Since the active ingredients thereof are amino acid (peptide) and vitamin, the present invention has less fear of causing side effects, is superior in safety, and can be consecutively used every day.

Where a numerical limit or range is stated herein, the endpoints are included. Also, all values and subranges within a numerical limit or range are specifically included as if m explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An anti-fatigue composition, comprising (1) histidine and (2) vitamin B6 in combination,
 wherein:
 said composition is contained in a unit package;
 said histidine is present in said unit package in an amount of not less than 0.5 g per said unit package; and
 said vitamin B6 is present in said unit package in an amount of not less than 15 mg per said unit package and said histidine and said vitamin B6 are present in a histidine:vitamin B6 weight ratio of about 120:1.

2. The composition according to claim 1, further comprising carnosine.

3. The composition according to claim 2, which comprises said histidine and said carnosine in a histidine:carnosine weight ratio of about 1:4.

4. The composition according to claim 1, wherein said unit package comprises written indicia that the amount of histidine to be ingested is not less than 0.05 g.

5. The composition according to claim 1, further comprising at least one kind of additive selected from the group consisting of an excipient, a corrigent, and a flavor.

6. The composition according to claim 1, which is in the form of a solid, a semi-solid, or a liquid.

7. The composition according to claim 1, which is in the form of a powder, a tablet, granule, or a capsule.

8. The composition according to claim 1, which is in the form of a slurry, a solution, a jelly, or an emulsion.

9. A method for treating, improving, or recovering from fatigue, comprising administering to a subject in need thereof an effective amount of a composition according to claim 1.

10. The method according to claim 9, wherein said composition further comprises carnosine.

11. A container-packed food, comprising (1) histidine and (2) vitamin B6,
 wherein:
 said histidine is present in said container in an amount of not less than 0.5 g; and
 said vitamin B6 is present in said container in an amount of not less than 15 mg and said histidine and said vitamin B6 are present in a histidine:vitamin B6 weight ratio of about 120:1.

12. The container-packed food according to claim 11, further comprising carnosine.

13. The container-packed food according to claim 12, wherein said container comprises written indicia that the amount of histidine to be ingested is not less than 0.5 g.

14. The container-packed food according to claim 11, further comprising at least one kind of additive selected from the group consisting of an excipient, a corrigent, and a flavor.

15. The container-packed food according to claim 11, which is in the form of a solid, a semi-solid, or a liquid.

16. The container-packed food according to claim 11, which is in the form of a powder, a tablet, a granule or a capsule.

17. The container-packed food according to claim 11, which is in the form of a slurry, a solution, a jelly or an emulsion.

18. The container-packed food according to claim 11, which is in a unit package form for a single administration of said food.

19. A container-packed food according to claim 11, which is a drink.

20. The container-packed food according to claim 19, further comprising carnosine.

21. The container-packed food according to claim 19, wherein said histidine is present in an amount of not less than 1 w/v %.

22. The container-packed food according to claim 19, which is in a unit package form.

23. An anti-fatigue composition, consisting of:
 (a) histidine;
 (b) vitamin B6; and
 (c) one or more ingredients selected from the group consisting of ascorbic acid, a salt of ascorbic acid, tartaric acid, a salt of tartaric acid, citric acid, a salt of citric acid, malic acid, a salt of malic acid, aspartame, stevia, sucralose, glycyrrhizinic acid, thaumatin, acesulfame potassium, saccharin, saccharin sodium, L-menthol, orange oil, lemon oil, lime oil, grapefruit oil, a flower essential oil, peppermint oil, spearmint oil, spice oil, lactose, sucrose, D-mannitol, starch, cornstarch, crystalline cellulose, light anhydrous silicic acid, magnesium stearate, calcium stearate, talc, and colloidal silica.

24. The anti-fatigue composition according to claim 23, wherein
   said histidine is present in a unit package in an amount of not less than 0.5 g per said unit package; and
   said vitamin B6 is present in said unit package in an amount of not less than 15 mg per said unit package; and
   said histidine and said vitamin B6 are present in a histidine:vitamin B6 weight ratio of 90:1 to 120:1.

25. The anti-fatigue composition according to claim 23, wherein said histidine and said vitamin B6 are present in a histidine:vitamin B6 weight ratio of about 120:1.

\* \* \* \* \*